United States Patent
Hirt et al.

(10) Patent No.: US 11,118,159 B2
(45) Date of Patent: Sep. 14, 2021

(54) COMPOSITIONS AND METHODS FOR PROVIDING PLANTS WITH TOLERANCE TO ABIOTIC STRESS CONDITIONS

(71) Applicant: King Abdullah University of Science and Technology, Thuwal (SA)

(72) Inventors: Heribert Hirt, Thuwal (SA); Axel de Zelicourt, Thuwal (SA); Maged Saad, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 94 days.

(21) Appl. No.: 16/072,137

(22) PCT Filed: Jan. 20, 2017

(86) PCT No.: PCT/IB2017/050314
§ 371 (c)(1),
(2) Date: Jul. 23, 2018

(87) PCT Pub. No.: WO2017/125894
PCT Pub. Date: Jul. 27, 2017

(65) Prior Publication Data
US 2019/0021342 A1   Jan. 24, 2019

Related U.S. Application Data

(60) Provisional application No. 62/281,404, filed on Jan. 21, 2016.

(51) Int. Cl.
| | | |
|---|---|---|
| *A01N 63/20* | (2020.01) | |
| *C12N 1/20* | (2006.01) | |
| *A01H 5/10* | (2018.01) | |
| *C12R 1/01* | (2006.01) | |
| *C12R 1/05* | (2006.01) | |
| *C12R 1/12* | (2006.01) | |

(52) U.S. Cl.
CPC ............... *C12N 1/205* (2021.05); *A01H 5/10* (2013.01); *A01N 63/20* (2020.01); *C12N 1/20* (2013.01); *C12R 2001/01* (2021.05); *C12R 2001/05* (2021.05); *C12R 2001/12* (2021.05)

(58) Field of Classification Search
CPC combination set(s) only.
See application file for complete search history.

(56) References Cited

U.S. PATENT DOCUMENTS

2015/0373993 A1   12/2015  Maltzahn

FOREIGN PATENT DOCUMENTS

| CA | 2953466 | 12/2015 |
| JP | 51446766 | 11/1979 |
| JP | 5702081 | 4/1982 |
| WO | 2015/091967 | 6/2015 |
| WO | 2017/125894 | 7/2017 |

OTHER PUBLICATIONS

Hayat, R. et al., Ann. Microbiol. 2010 vol. 60, pp. 579-598.*
Andres-Barrao, et al., "Complete Genome Sequence Analysis of *Enterobacter* sp. SA187, a Plant Multi-Stress Tolerance Promoting Endophytic Bacterium", *Front Microbiol*, 8:1-21 (2017).
Bolger, et al., "Trimmomatic: a flexible trimmer for Illumina sequence data", *Bioinformatics*, 30:2114-2120 (2014).
Chaves, et al., "How plants cope with water stress in the field. Photosynthesis and growth", *Ann Bot*, 89:907-916 (2002).
Chen, et al. "Application of Plant growth-promoting endophytes (PGPE) isolated from *Solanum nugrum* L. for phytoextraction of Cd-polluted soils", *Apl. Soil Ecol.*, 46(3):383-389 (2010).
Coleman-Derr, et al., "Building the crops of tomorrow: advantages of symbiont-based approaches to improving abiotic stress tolerance", *Front Microbiol.*, 5:283 (2014).
De Zelicourt, "Rhizosphere microbes as essential partners for plant stress tolerance", et al., *Mol Plant*, 6:242-245 (2013)).
Deinlein, et al., "Plant salt-tolerance mechanisms", *Trends Plant Sci*, 19:371-379 (2014).
Eckert, et al., "Ethylene-forming enzyme and bioethylene production", *Biotechnol Biofuels*, 7:33 (2014).
Gao, et al., "Symbiotic adaptation drives genome streamlining of the cyanobacterial sponge symbiont Candidatus Synechococcus spongiarum", *MBio*, 5(2)e0079-14, (2014).
Glick, et al., "Plant Growth-Promoting Bacteria: Mechanisms and Applications", *Scientifica*, 2012:1-15 (2012).
Guzmán, et al., "Exploiting the triple response of *Arabidopsis* to identify ethylene-related mutants", *Plant Cell*, 2:513-523 (1990).
Han, et al., "Beneficial soil bacterium Bacillus subtilis (GB03) augments salt tolerance of white clover", *Front Plant Sci*, 5:525 (2014).
Hanin et al., "New Insights on Plant Salt Tolerance Mechanisms and Their Potential Use for Breeding", *Front Plant Sci.*, 7:1-17 (2016).
Hossain, et al., "One-step biosynthesis of $\alpha$-keto-$\gamma$-methylthiobutyric acid from L-methionine by an *Escherichia coli* whole-cell biocatalyst expressing an engineered L-amino acid deaminase from Proteus vulgaris", *PLOS One*, 9(12):e114291 (2014).
Kaplan, et al., "A survey of the microbial community in the rhizosphere of two dominant shrubs of the Negev Desert highlands, Zygophyllum dumosum (Zygophyllaceae) and Atriplex halimus (Amaranthaceae), using cultivation-dependent and cultivation-independent methods", *Am J Bot*, 100:1713-1725 (2013).

(Continued)

*Primary Examiner* — Heidi Reese
(74) *Attorney, Agent, or Firm* — Pabst Patent Group LLP

(57) ABSTRACT

It has been discovered that the desert endophytic bacterium SA187 SA187 can provide resistance or tolerance to abiotic stress conditions to seeds or plants. Compositions containing SA187 can be used to enhance plant development and yield under environmental stress conditions.

11 Claims, 14 Drawing Sheets

Specification includes a Sequence Listing.

(56) References Cited

OTHER PUBLICATIONS

Karlidag, et al., "Plant Growth-promoting Rhizobacteria Mitigate Deleterious Effects of Salt Stress on Strawberry Plants (*Fragaria xananassa*)", *Hortic Sci*, 48:563-567 (2013).

Konishi and Yanagisawa, ",Ethylene signaling in Arabidopsis involves feedback regulation via the elaborate control of EBF2 expression by EIN3", *Plant J*, 55:821-831 (2008).

Lafi, et al., "Draft Genome Sequence of the Plant Growth-Promoting Rhizobacterium Acinetobacter radioresistens Strain SA188 Isolated from the Desert Plant *Indigofera argentea*", *Genome Announc*, 9-10 (2017).

Marasco, et al., "A drought resistance-promoting microbiome is selected by root system under desert farming", *PLoS One*, 7:e48479 (2012).

Nadeem, et al., "Variation in growth and ion uptake of maize due to inoculation with plant growth promoting rhizobacteria under salt stress", *Microbiology*, 25:78-84 (2006).

Negrao et al., "Evaluating physiological responses of plants to salinity stress", Ann Bot, 119:1-11 (2017).

Park et al., "Abscisic acid inhibits type 2C protein phosphatases via the PYR/PYL family of START proteins", Science, 324:1068-1071 (2009).

Rifat, et al., "Soil beneficial bacteria and their role in plant growth promotion: a review", *Annals of Microbiol.*, 60(4):579-598 (2010).

Roman, et al., "Genetic analysis of ethylene signal transduction in *Arabidopsis thaliana*: five novel mutant loci integrated into a stress response pathway", *Genetics*, 139:1391-1409 (1995).

Schwartz, et al., "Biochemical characterization of the aba2 and aba3 mutants in *Arabidopsis thaliana*", *Plant Physiol*, 114 :161-166 (1997).

Shabala, et al., "Learning from halophytes: physiological basis and strategies to improve abiotic stress tolerance in crops", *Ann Bot*, 112:1209-1221 (2013).

Singh and Jha, "Boosting Alfalfa (*Medicago sativa* L.) Production With Rhizobacteria From Various Plants in Saudi Arabia", *Acta Physiol Plant*, 38:110 (2016).

Staswick, et al., "Methyl jasmonate inhibition of root growth and induction of a leaf protein are decreased in an *Arabidopsis thaliana* mutant", *Proc Natl Acad Sci USA*, 89 :6837-6840 (1992).

Sun, et al., "Potassium Retention under Salt Stress Is Associated with Natural Variation in Salinity Tolerance among *Arabidopsis* Accessions", *PLoS One*, 10:e0124032 (2015).

Trapnell, et al., "Transcript assembly and quantification by RNA-Seq reveals unannotated transcripts and isoform switching during cell differentiation", *Nat Biotechnol*, 28:511-515 (2010).

Zhang, et al., "Soil bacteria confer plant salt tolerance by tissue-specific regulation of the sodium transporter HKT1", *Mol Plant-Microbe Interact*, 21:737-744 (2008).

Arshad, et al., "Kinetics and effects of trace elements and electron complexes on 2-keto-4-methylthiobutyric acid-dependent biosynthesis of ethylene in soil", Letters in Applied Microbiology, 39(3):306-309 (2004).

Martensson, "The occurrence of 4-methylthio-2-hydroxybutyrate in human urine", Analytical Biochemistry, 154(1):43-49 (1986).

Sunaina, et al., "Bacterial Metabolites from Bacillus Cereus B4 Responsible for Potato Plant Growth", Potato J., 32(3-4):167-188 (2005).

* cited by examiner

Figure 1. Yield losses of eight representative crops due to environmental stress. Average yields and losses caused by abiotic and biotic stresses are illustrated as a percentage of the record yield obtained for each of the crops: maize, wheat, soybean, sorghum, oat, barley, potato and sugar beet. Data taken from Buchanan et al. (2000).

COMPOSITIONS AND METHODS FOR PROVIDING PLANTS WITH TOLERANCE TO ABIOTIC STRESS CONDITIONS

CROSS-REFERENCE TO RELATED APPLICATIONS

This application is a National Phase application under 35 U.S.C. § 371 of International Application No. PCT/IB2017/050314, filed on Jan. 20, 2017, entitled "COMPOSITIONS AND METHODS FOR PROVIDING PLANTS WITH TOLERANCE TO ABIOTIC STRESS CONDITIONS", which claims benefit of and priority to U.S. Provisional Patent Application No. 62/281,404 filed on Jan. 21, 2016, and are incorporated herein in its their entirety.

FIELD OF THE INVENTION

The invention is generally directed to bacterial compositions and methods of use to increase abiotic stress tolerance or resistance in plants.

REFERENCE TO SEQUENCE LISTING

The Sequence Listing submitted Jan. 20, 2017, as a text file named "KAUST_ST25.txt" created on Jan. 20, 2017, and having a size of 5.4 KB is hereby incorporated by reference pursuant to 37 C.F.R. § 1.52(e)(5).

BACKGROUND OF THE INVENTION

The United Nations predicts that the world population will reach 8.5 billion by 2030 (UN News Centre, 2015). A key challenge for feeding the world population is the global water shortage which limits crop yields in more than 70% of arable lands (Timmusk, S. et al., PLOS One, 9(5) 1-13 (2014)). Abiotic stresses, such as drought, heat and salt, are the most important limiting factors in agriculture not only in Saudi Arabia but worldwide. These environmental stresses are the cause of more than 50% of crop losses globally (FIG. 1). Therefore, major efforts are underway on improving plant stress tolerance by molecular breeding and genetic manipulation (GM) techniques. However, these processes are long term investments of high costs and require extensive registration procedures before marketing of the products is possible.

An alternative approach to improve plant stress tolerance has been largely overlooked in the past decades is to make use of rhizosphere microbes which offer a cheap GM-free alternative.

Therefore, it is an object of the invention to provide compositions and methods for providing plants with resistance or tolerance to abiotic stress conditions.

It is another object of the invention to provide seed coating compositions that provide plants with resistance or tolerance to abiotic stress conditions.

It is still another object to provide methods for growing plants under abiotic stress conditions.

SUMMARY OF THE INVENTION

It has been discovered that *Enterobacter* sp. SA187 (hereafter named SA187) can provide resistance or tolerance to abiotic stress conditions to seeds or plants. Compositions containing SA187 can be used to enhance plant development and yield under environmental stress conditions. One embodiment provides an isolated culture of SA187. In another embodiment, the SA187 is genetically modified to express one or more heterologous genes or proteins.

The desert endophytic bacterium SA187 confers abiotic stress tolerance and enhances yield and biomass production of model and crop plants, respectively, using a 2-keto-4-methylbutyric acid (KMBA) dependent ethylene signaling activation. SA187 was found to colonize both surface and inner plant root and shoot tissues and to modify several plant phytohormone pathways. Transcriptome and genetic studies showed that the ethylene signaling pathway was the major contributor for mediating abiotic stress tolerance by SA187. Interestingly, neither plants nor SA187 produce ethylene directly, but upon colonization, plants induce expression of the methionine salvage pathway in SA187 to produce KMBA that is subsequently converted to ethylene in planta. These results reveal a complex molecular communication process during beneficial plant-microbe interactions and prove the potential of beneficial microbes for strengthening agriculture under adverse environmental conditions.

One embodiment provides a plant substrate containing an effective amount of *Enterobacter* sp. SA187 to inhibit or reduce abiotic stress in the plant. In a preferred embodiment suitable plant substrates include, but are not limited to soil, peat, compost, vermiculite, perlite, sand, clay and combinations thereof.

Still another embodiment provides a non-desert plant inoculated with an amount of SA187 to provide abiotic stress tolerance, enhance yield, enhance biomass, or a combination thereof. Preferred non-desert plants include, but are not limited to crop plants that are not indigenous to desert environment.

The disclosed compositions and methods can provide tolerance or resistance to abiotic stress conditions including, but not limited to drought, high heat, high salt, bright light, ultraviolet light, too high and too low temperatures, freezing, heavy metals and hypoxia.

Still another embodiment provides a plant substrate inoculated with SA187 and one or more additional plant growth-promoting bacteria and/or one or more plant growth-promoting rhizobacteria. Exemplary additional plant growth-promoting bacteria or rhizobacteria include but are not limited to *Pseudomonas putida, Pseudomonas aeruginosa, Klebsiella* sp., *Enterobacter asburiae, Rhizobium* sp. (pea), *Mesorhizobium* sp., *Acinetobacter* spp., *Rhizobium* sp. (lentil), *Pseudomonas* sp. A3R3, *Psychrobacter* sp. SRS8, *Bradyrhizobium* sp., *Pseudomonas aeruginosa* 4EA, *Pseudomonas* sp., *Ochrobactrum cytisi, Bacillus* species PSB10, *Paenibacillus polymyxa, Rhizobium phaseoli, Rahnella aquatilis, Pseudomonas fluorescens, Ralstonia metallidurans, Azospirillum amazonense, Serratia marcescens, Enterobacter* sp., *Burkholderia, Pseudomonas jessenii, Azotobacter* sp., *Mesorhizobium ciceri, Azotobacter chroococcum, Klebsiella oxytoca, Pseudomonas chlororaphis, Bacillus subtilis, Gluconacetobacter, diazotrophicus, Brevibacillus* spp., *Bravibacterium* sp., *Xanthomonas* sp. RJ3, *Azomonas* sp. RJ4, *Pseudomonas* sp. RJ10, *Bacillus* sp. RJ31, *Bradyrhizobium japonicum, Variovorax paradoxus, Rhodococcus* sp., *Flavobacterium, Sphingomonas* sp, *Mycobacterium* sp, *Rhodococcus* sp, *Cellulomonas* sp., *Azospirillum* sp., *Azospirillum brasilense, Rhizobium meliloti, Kluyvera ascorbata, Rhizobium cicero, Rhizobium leguminosarum, Paenibacillus polymyxa* strain A26, a *Alcaligenes faecalis* strain AF, and combinations thereof.

Yet another embodiment provides a plant seed coated with an effective amount of SA187 to provide the seed with resistance to abiotic stress conditions as the seed grows. The coating can contain one or more additional plant growth-promoting bacteria or rhizobacteria.

Another embodiment provides a plant root coated with SA187 optionally including one more additional plant growth-promoting bacteria or rhizobacteria.

Still another embodiment provides a method of providing a seed or plant with resistance to abiotic stress conditions by coating the seed or a root of the plant with an effective amount of SA187 to provide the seed or plant with resistance to the abiotic stress conditions.

Yet another embodiment provides a method of improving growth of a seed or plant under abiotic stress conditions by growing the seed or plant in a plant substrate, wherein the plant substrate comprises an effective amount of SA187 to colonize the seed or a root of the plant to provide abiotic stress resistance to the seed or plant.

Another embodiment provides a method of improving tolerance of a seed or plant to abiotic stress conditions by coating the seed or root of the plant with an effective amount of SA187 to provide the plant with resistance to abiotic stress.

Still another embodiment provides a method of improving tolerance of a seed or plant against abiotic stress conditions by growing the seed or plant in a plant substrate comprising an effective amount of SA187 to provide the seed or plant with tolerance to the abiotic stress conditions.

Yet another embodiment provides a method of providing a plant with abiotic stress resistance by inoculating the plant's rhizosphere with SA187.

Another embodiment provides a seed coating composition containing SA187. The SA187 can be encapsulated with a non-toxic, biodegradable coating. The seed coating composition can also contain a coating adhesive. Exemplary seed coating compositions contain gelatin, cellulose, alginate, xanthum, or a combination thereof. Certain seed coating compositions can have multiple layers.

One embodiment provides SA187 whose genome contains SEQ ID NO:1, 2, 3, 4, 5, 6, 7, 8, 9, 10, 11, 12, 13, or a combination thereof. In still another embodiment provides SA187 whose genome contains all of SEQ ID NO:1-13.

BRIEF DESCRIPTION OF THE DRAWINGS

FIG. 8D is a graph of phenotype and FIG. 8F is a bar graph of heat survival rate of one-week-old SA187-colonized or mock-treated *Arabidopsis* seedlings exposed to heat stress. FIGS. 8H and 8KI are graphs showing growth parameters of SA187-colonized 25-day-old field-grown alfalfa plants using 2 water regimes, normal and high salinity. Percentages indicate improvement of SA187-colonized plants compared to mock-treated plants. Asterisks indicate statistical difference based on the Mann-Whitney test between mock- and SA187-treated plants under the same conditions (P<0.01, *P<0.001).

DETAILED DESCRIPTION OF THE INVENTION

I. Definitions

Figure 1:
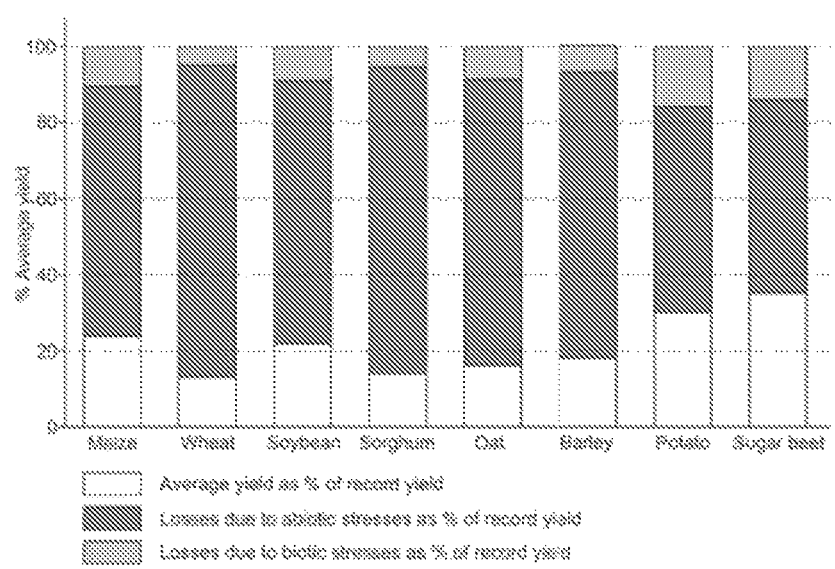
FIG. 1 is bar graph of various crops showing the percent average yield for average yield as % of record (open box), losses due to abiotic stresses as a % of record yield (solid black box), and losses due to biotic stresses as % of record (solid grey box). Data taken from Buchanan et al., Am Soc Plant Physiol. 1367 (2000).

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "plant substrate" refers to a substrate commonly used for growing plants, including plant seeds, plant roots and plant seedlings. Non-limiting examples of such plant substrates include, but are not limited to soil, peat, compost, vermiculite, perlite, sand, clay, and combinations thereof.

"Plant growth-promoting rhizobacteria (PGPR)" refers soil bacteria that colonize the roots of plants following inoculation onto seed and that enhance plant growth (Kloepper, Joseph W.; Schroth, Milton N., Proceedings of the 4th International Conference on Plant Pathogenic Bacteria (Angers, France: Station de Pathologie Végétale et Phytobactériologie, INRA) 2: 879-882 (1978); Aziz, Z. F. A., et al., Malaysian Journal of Microbiology 8(1): 47-50 (2012)).

"Abiotic stress conditions" refer to conditions caused by non-living factors on the living organisms in a specific environment. Exemplary abiotic stress conditions include, but are not limited to drought, high heat, high salt, bright light, ultraviolet light, too high and too low temperatures, freezing, heavy metals and hypoxia. High salt concentrations typically refers to 100-300 mM salt (such as NaCl) or higher. Saline soil has an excess of soluble salt in the soil solution, the liquid located between aggregates of soil. A sodic soil has too much sodium associated with the negatively charged clay particles. Salinity occurs through natural or human-induced processes that result in the accumulation of dissolved salts in the soil water to an extent that inhibits plant growth. Natural salinity results from the accumulation of salts over long periods of time and is caused by two natural processes. The first is the weathering process that breaks down rock and release soluble salts of various type, mainly chloride of sodium, calcium and magnesium, and to a lesser extent, sulphates and carbonates. Sodium chloride is the most soluble salt. The second is the deposition of oceanic salt carried in wind and rain. Human-induced salinity results from human activity that change the hydrologic balance of the soil between water applied (irrigation or rainfall) and water used by crops (transpiration). The most common causes are (i) land clearing and the replacement of perennial vegetation with annual crops, and (ii) irrigation schemes using salt-rich irrigation water or having insufficient drainage (Roberto (2011). Soil Bacteria Support and Protect Plants Against Abiotic Stresses, Abiotic Stress in Plants—Mechanisms and Adaptations, Prof. Arun Shanker (Ed.), ISBN: 978-953-307-394-1, InTech, DOI: 10.5772/23310). With regard to heat, a transient elevation in temperature, usually 10-15° C. above ambient, is considered stress, but heat stress also depends on temperature intensity, duration of treatment and rate of temperature increase.

II. Compositions for Promoting Abiotic Stress Resistance

Compositions containing SA187 are provided that can be used to provide seeds and plants with resistance or tolerance to abiotic stress conditions. *Enterobacter* sp. SA187 is an endophytic bacteria isolated from surface sterilized root nodules formed on roots of pioneer plant *Indigofera argentea* Burm.f. (Fabaceae). SA187 was deposited on Sep. 24, 2019, with American Type Culture Collection (ATCC), P.O. Box 1549, Manassas, Va. 20110 USA, and given Patent Deposit Number PTA-126210. Preferred seeds and plants, preferably roots that can be inoculated with or coated with SA187 include, but are not limited to alfalfa, cotton, wheat, maize, soybean, oat, barley, potato, and sugar beets.

One embodiment provides seeds or plants inoculated with an effective amount of SA187 to provide the seed or plant with resistance or tolerance to abiotic stress conditions. The seeds or plants can be coated with SA187. One embodiment provides a root of a plant coated with SA187.

A. SA187 Containing Plant Substrates

Rhizosphere microorganisms, particularly beneficial bacteria and fungi, can improve plant performance under stress environments and, consequently, enhance yield both directly and indirectly (C. Dimkpa, et al, Plant, Cell and Environment, 32 1682-1694 (2009)). Some plant growth-promoting rhizobacteria (PGPR) may exert a direct stimulation on plant growth and development by providing plants with fixed nitrogen, phytohormones, iron that has been sequestered by bacterial siderophores, and soluble phosphate (R. Hayat, et al., Annals of Microbiology, 60 579-598 (2010)). Others do this indirectly by protecting the plant against soil-borne diseases, most of which are caused by pathogenic fungi (B. Lutgtenberg and F. Kamilova, Annual Review of Microbiology, 63 541 556 (2009)).

Bacteria of diverse genera such as *Arthrobacter, Azotobacter, Azospirillum, Bacillus, Enterobacter, Pseudomonas* and *Serratia* (E. J. Gray and D. L. Smith, Soil Biology & Biochemistry, 37 395 412 (2005)), as well as *Streptomyces* spp. (Dimkpa, C. et al., Canadian Journal of Microbiology, 54:163 172 (2008)) have been identified as PGPR and can be combined with SA187 in the disclosed compositions.

One embodiment provides a plant substrate containing an effective amount of a species of the genus *Enterobacter* to inhibit or reduce abiotic stress in the plant. In a preferred embodiment, the *Enterobacter* species is SA187. Suitable plant substrates include, but are not limited to soil, peat, compost, vermiculite, perlite, sand, clay and combinations thereof. Typically, the plant substrates contain $10^6$ to $10^9$ bacteria per/g of substrate.

B. Co-Inoculation

Plants and seeds can be co-inoculated with SA187 and one or more other plant growth-promoting bacteria or rhizobacteria to provide the seeds or plants with resistance or tolerance to abiotic stress conditions. Co-inoculation is based on mixed inoculants, combination of microorganisms that interact synergistically, or when microorganisms such as *Azospirillum* are functioning as "helper" bacteria to enhance the performance of other beneficial microorganisms. In the rhizosphere the synergism between various bacterial genera such as *Bacillus, Pseudomonas* and *Rhizobium* has been demonstrated to promote plant growth and development. Compared to single inoculation, co-inoculation can improve the absorption of nitrogen, phosphorus and mineral nutrients by plants.

Suitable bacteria that can be co-inoculated with SA187 include but are not limited to *Pseudomonas putida, Pseudomonas aeruginosa, Klebsiella* sp., *Enterobacter asburiae, Rhizobium* sp. (pea), *Mesorhizobium* sp., *Acinetobacter* spp., *Rhizobium* sp. (lentil), *Pseudomonas* sp. A3R3, *Psychrobacter* sp. SRS8, *Bradyrhizobium* sp., *Pseudomonas aeruginosa* 4EA, *Pseudomonas* sp., *Ochrobactrum cytisi, Bacillus* species PSB10, *Paenibacillus polymyxa, Rhizobium phaseoli, Rahnella aquatilis, Pseudomonas fluorescens, Ralstonia metallidurans, Azospirillum amazonense, Serratia marcescens, Enterobacter* sp., *Burkholderia, Pseudomonas jessenii, Azotobacter* sp., *Mesorhizobium ciceri, Azotobacter chroococcum, Klebsiella oxytoca, Pseudomonas chlororaphis, Bacillus subtilis, Gluconacetobacter, diazotrophicus, Brevibacillus* spp., *Bravibacterium* sp., *Xanthomonas* sp. RJ3, *Azomonas* sp. RJ4, *Pseudomonas* sp. RJ10, *Bacillus* sp. RJ31, *Bradyrhizobium japonicum, Variovorax paradoxus, Rhodococcus* sp., *Flavobacterium, Sphingomonas* sp, *Mycobacterium* sp, *Rhodococcus* sp, *Cellulomonas* sp., *Azospirillum* sp., *Azospirillum brasilense, Rhizobium meliloti, Kluyvera ascorbata, Rhizobium cicero, Rhizobium leguminosarum, Paenibacillus polymyxa* strain A26, a *Alcaligenes faecalis* strain AF, and combinations thereof.

Additional bacteria that can be inoculated with SA187 and exemplary plants that can be inoculated include those listed in Table 1.

TABLE 1

Bacterial Inoculates for Abiotic Stress (From Bianco Carmen and Defez Roberto (2011). Soil Bacteria Support and Protect Plants Against Abiotic Stresses, Abiotic Stress in Plants - Mechanisms and Adaptations, Prof. Arun Shanker (Ed.), ISBN: 978-953-307-394-1, InTech, DOI: 10.5772/23310)

| Stress type | Bacterial inoculate | Plant Species |
| --- | --- | --- |
| Salt | *Pseudomonas pseudoalcaligenes, Bacillus pumilus* | Rice (*Oryza sativa*) |
| Salt | *Bacillus megaterium* | Maize (*Zea maize* L.) |
| Salt | *Azospirillum brasilense* | Barley (*Hordeum vulgare*) |
| Salt | *Pseudomonas mendocina* | Lettuce (*L. sativa* L. cv. *Tafalla*) |
| Salt | *Azospirillum* sp. | Pea (*Phaseolus vulgaris*) |
| Salt | *Bacillus subtilis* | *Arabidopsis thaliana* |

TABLE 1-continued

Bacterial Inoculates for Abiotic Stress (From Bianco Carmen and Defez Roberto (2011). Soil Bacteria Support and Protect Plants Against Abiotic Stresses, Abiotic Stress in Plants - Mechanisms and Adaptations, Prof. Arun Shanker (Ed.), ISBN: 978-953-307-394-1, InTech, DOI: 10.5772/23310)

| Stress type | Bacterial inoculate | Plant Species |
| --- | --- | --- |
| Salt | *Pseudomonas syringae, Pseudomonas fluorescens, Enterobacter aerogenes* | Maize (*Zea maize*) |
| Salt | *P. fluorescens* | Groundnut (*Arachis hypogaea*) |
| Salt | *Azospirillum* | Lettuce (*Lactuca sativa*) |
| Salt | *Achromobacter piechaudii* | Tomato (*Lycopersicon esculentum*) |
| Salt | *Aeromonas hydrophila/caviae Bacillus insolitus, Bacillus* sp. | Wheat (*Triticum aestivum*) |
| Salt | *Azospirillum* | Maize (*Z. maize*) |
| Salt | *A. brasilense* | Chickpeas (*Cicer arietinum*), faba beans (*Vicia faba* L.) |
| Drought | *Pseudomonas* spp. | Maize (*Zea mays* L. cv. Kaveri) |
| Drought | *Pseudomonas* spp. | Asparagus (*Asparagus officinalis* L.) |
| Drought | *Pseudomonas mendocina* | Lettuce (*Lactuca sativa* L.) |
| Drought | *Rhizobium tropici, Paenibacillus polymyxa* | Common bean (*Phaseolus vulgaris* L.) |
| Drought | *Bacillus* | Lettuce (*Lactuca sativa* L.) |
| Drought | *Ensifer meliloti* bv. *mediterranense* | Bean (*Phaseolus vulgaris* cv. Flamingo) |
| Drought | *Bradyrhizobium elkanii* | Flat crown (*Albizia adianthifolia*) |
| Drought | *Achromobacter piechaudii* | Tomato (*L. esculentum*), pepper (*Capsicum annuum*) |
| Drought | *Azospirillum* | Wheat (*T. aestivum*) |
| Drought | *A. brasilense* | Maize (*Z. mays*) |
| Drought | *A. brasilense* | Common bean (*P. vulgaris*) |
| Osmotic stress | *Bacillus subtilis* | Arabidopsis |
| Osmotic stress | *A. brasilense* | Rice (*Oryza sativa* L.) |
| Osmotic stress (45% PEG) | *Arthrobacter* sp., *Bacillus* sp. | Pepper (*C. annuum*) |
| Osmotic stress (20% PEG) | *Azospirillum* | Wheat (*T. aestivum*) |
| Flooding | *Enterobacter cloacae, Pseudomonas putida* | Tomato (*L. esculentum*) |
| Temperature | *Burkholderia phytofirmans* | Grapevine (*Vitis vinifera*) |
| Temerature | *Pseudomonas fluorescens, Pantoea agglomerans, Mycobacterium* sp. | Wheat (*Triticum aestivum*) |
| Temperature | *B. phytofirmans* | Potato (*Solanum tuberosum*) |
| Temperature | *Aeromonas hydrophila, Serratia liquefaciens, Serratia proteamaculans* | Soy bean (*Glycine max*) |
| Temperature | *Burkholderia phytofirmans* | Grapevine (*Vitis vinifera*) |
| Temperature | *B. phytofirmans* | Potato (*Solanum tuberosum*) |
| Temperature | *Aeromonas hydrophila, Serratia liquefaciens, Serratia proteamaculans* | Soy bean (*Glycine max*) |
| Nutrient deficiency | *Azospirillum* sp., *Azotobacter chroococcum, Mesorhizobium ciceri, Pseudomonas fluorescens* | Chickpea (*Cicer arietinum* L.) |
| Nutrient deficiency | *Azotobacter coroocoocum, Azospirillum brasilens, Pseudomonas putida, Bacillus lentus* | Zea maize L. (*Zea maize* L.) |
| Nutrient deficiency | *Bacillus* sp., *Burkholderia* sp., *Streptomyces platensis* | Zea maize L. |
| Nutrient deficiency | *Bacillus* sp., | Zea maize L. |

TABLE 1-continued

Bacterial Inoculates for Abiotic Stress (From Bianco Carmen and Defez Roberto (2011). Soil Bacteria Support and Protect Plants Against Abiotic Stresses, Abiotic Stress in Plants - Mechanisms and Adaptations, Prof. Arun Shanker (Ed.), ISBN: 978-953-307-394-1, InTech, DOI: 10.5772/23310)

| Stress type | Bacterial inoculate | Plant Species |
|---|---|---|
| Nutrient deficiency | *Bacillus polymyxa*, *Mycobacterium phlei*, *Pseudomonas alcaligenes* | *Zea maize* L. (*Zea maize* cv. *Felix*) |
| Heavy metals toxicity | *Sanguibacter* sp., *Pseudomonas* sp. | *Nicotina tabacum* |
| Heavy metals toxicity | *Bacillus subtilis*, *Pantoea agglomerans* | Oat (*Avena sativa*) |
| Heavy metals toxicity | *Pseudomonas fluorescens*, *Microbacterium* sp. | Rape (*Brassica napus*) |
| Heavy metals toxicity | *Methylobacterium oryzae*, *Burkholderia* sp. | Tomato (*Lycopersicon esculentum* L.) |
| Heavy metals toxicity | *Bacillus subtilis*, *Bacillus megaterium*, *Bacillus* sp. | Rice (*O. sativa*) |

C. Seed Coating Compositions

One embodiment provides a seed coating composition having at least one layer coating all or part of the seed, wherein at least one layer contains an effective amount of SA187 to provide the seed or the plant that grows from the seed with resistance to abiotic stress conditions. The SA187 can be from $10^6$/ml to $10^9$/ml of seed coating composition.

Another embodiment provides a seed coating composition containing SA187. The SA187 can be encapsulated with a non-toxic, biodegradable coating. The seed coating composition can also contain a coating adhesive. Exemplary seed coating compositions contain gelatin, cellulose, alginate, xanthum, or a combination thereof. Certain seed coating compositions can have multiple layers.

In another embodiment, the seed coating composition contains multiple layers for example, 2, 3, 4 or 5 or more layers. SA187 and/or one or more additional plant growth promoting bacteria can be in any or all of the layers of the seed coating composition; however, at least one of the layers of a multiple layer seed coating composition contains an effective amount of SA187 to provide the seed or the plant growing from the seed with resistance to abiotic stress conditions. Preferably, the SA187 or other plant growth promoting bacteria are in the layer adjacent to the surface of the seed.

In one embodiment, at least one layer contains guar gum, derivative guar, polyacrylamide, poly(methacrylic acid), poly(acrylic acid), polyacrylate, poly(ethylene glycol), phosphonate-end capped polymers, polyethyleneoxide, poly(vinyl alcohol), polyglycerol, polytetrahydrofuran, polyamide, hydroxypropyl guar, carboxymethyl guar, carboxymethyl hydroxypropyl guar, starch, derivatized (e.g., cationic) starch, corn starch, wheat starch, rice starch, potato starch, tapioca, waxy maize, sorghum, waxy sarghum, sago, dextrin, chitin, chitosan, alginate compositions, xanthan gum, carageenan gum, gum karaya, gum arabic, pectin, cellulose, hydroxycellulose, hydroxyalkyl cellulose, hydroxyethyl cellulose, carboxymethylhydroxyethyl cellulose, hydroxypropyl cellulose, a derivative of any of the foregoing or a combination of any of the foregoing. As non-limiting examples, the layer can contain a 90 wt % derivatized guar and 10 wt % starch (or derivatized starch) mixture, or a 60 wt % hydroxypropyl guar and 40 wt % carboxymethyl hydroxypropyl guar mixture.

In some embodiments, the layer can act as a carrier coating. Fungicides and beneficial microbes that protect the seed and emerging seedling are carried in the carrier coating. For example, alfalfa seed coating with incorporated SA187 is used to inoculate the field in which desired crop plants are planted or are growing.

Another embodiment provides agglomerates of seed. The agglomerate or grouping of seed is a grouping of 2 or more individual seeds together. The seeds can be for the same plant or for different plants. In another embodiment, the agglomerate is a grouping of more than 5 individual seeds together. In a further embodiment, the agglomerate is a grouping of more than 10 individual seeds together. In yet another embodiment, the agglomerate is a grouping of more than 25 individual seeds together. In yet a further embodiment, the agglomerate is a grouping of more than 50 individual seeds together. In another embodiment, the agglomerate is a grouping of more than 100 individual seeds together.

1. Seed Agglomerates

The agglomeration of seed can aid in the application of the seed coating composition because the seed coating composition, when using an agglomeration of seed, can be shaped or formed to be consistent in shape or form. For example, the agglomeration can be formed as spherical or substantially spherical, thus allowing the seed coating composition to be likewise substantially spherical. This can allow for improved or more consistent casting or spraying, can minimize the occurrence of blockage or clogging of the nozzles, hoses, etc. due to uneven particle size distribution. Typically, a binder or adhesive is utilized to bunch (e.g., agglomerize) the grouping of seeds together.

The agglomeration can also aid in seed or seedling establishment as a layer of the wetting agent (or other layer than affects the soil) can be concentrated to a local area of soil, thus, increasing its chance of wetting the soil surrounding the seed(s). the agglomeration can also promote survival by allowing the seeds, when germinating into seedlings, to generate sufficient force to penetrate hydrophobic areas or soil such as, for example, a hydrophobic (i.e., encrusted) soil surface In one embodiment, the seed coating composition contains an agglomeration of seeds of from between 2 seeds to 100 seeds, typically between 2 to 50 seeds, typically between 2 to 25 seeds; and at least one layer selected from the group consisting a layer of a filler, a layer of a binding agent, a layer of a wetting agent, a layer of an anti-bacteria agent, a layer of an active ingredient and any combination thereof.

In one embodiment, the seed coating composition is of substantially uniform size of from between 10 micrometers and 4 mm in diameter. In another embodiment, the seed coating composition is of substantially uniform size of from between 25 micrometers and 2 mm in diameter. In a further, the seed coating composition is of substantially uniform size of from between 500 micrometers and 2 mm in diameter.

2. Binder

The seed coating composition can also contain a binder as one of the layers, the binder is sometimes referred to as an adhesive. In one embodiment, the binder can include but is not limited to molasses, granulated sugar, alginates, karaya gum, guar gum, tragacanth gum, polysaccharide gum, mucilage or any combination of the foregoing. In another embodiment, the binder is chosen from, but is not limited to, gelatin, polyvinyl acetates, polyvinyl acetate copolymers, polyvinyl alcohols, polyvinyl alcohol copolymers, celluloses (including ethylcelluloses and methylcelluloses, hydroxypropylcelluloses, hydroxymethyl celluloses, hydroxymethylpropyl-celluloses), polyvinylpyrolidones, dextrins, malto-dextrins, polysaccharides, fats, oils, proteins, gum arabics, shellacs, vinylidene chloride, vinylidene chloride copolymers, calcium lignosulfonates, acrylic copolymers, starches, polyvinylacrylates, zeins, carboxymethylcellulose, chitosan, polyethylene oxide, acrylimide polymers and copolymers, polyhydroxyethyl acrylate, methylacrylimide monomers, alginate, ethylcellulose, polychloroprene, syrups or any combination of the foregoing.

3. Active Ingredients

The seed coating compositions can also include one or more active ingredients in one or more of the layers of the coating. Compounds suitable as active ingredients, which in some embodiments form all or part of at least one layer of the seed coating composition, include but are not limited to herbicides, plant growth regulators, crop desiccants, fungicides, insecticides, insect repellants, and combinations thereof. Suitable pesticides include, for example, triazine herbicides; sulfonylurea herbicides; uracils; urea herbicides; acetanilide herbicides; and organophosphonate herbicides such as glyphosate salts and esters. Suitable fungicides include, for example, nitrilo oxime fungicides; imidazole fungicides; triazole fungicides; sulfenamide fungicides; dithio-carbamate fungicides; chloronated aromatic; and dichloro aniline fungicides. Suitable insecticides, include, for example, carbamate insecticides; organo thiophosphate insecticides; and perchlorinated organic insecticides such as methoxychlor. Suitable miticides include, for example, propynyl sulfite; triazapentadiene miticides; chlorinated aromatic miticides such as tetradifan; and dinitrophenol miticides such as binapacryl. Other active ingredients can include adjuvants, surfactants, and fertilizers.

4. Filler

The seed coating composition can also include at least one filler as all or part of a layer. In one embodiment, the filler is selected from the group consisting of wood flours, clays, activated carbon, carbohydrates, sugars, dextrins, maltodextrins, diatomaceous earth, cereal flours, wheat flour, oat flour, barley flour, fine-grain inorganic solids, calcium carbonate, calcium bentonite, kaolin, china clay, talc, perlite, mica, vermiculite, silicas, quartz powder, montmorillonite or mixtures thereof.

5. Nutrients

The seed coating composition can also contain a nutrient such as a micronutrient or macronutrient in one or more layers of the seed coating composition. The nutrient can be in all or part of a layer. The nutrient can also be included with the grouping of seeds as part of the binder or adhesive. "Nutrient" as used herein can refer to an additive or substance utilized by plants, grasses, shrubs for plant, grass, and shrub growth, respectively. Macronutrients can be utilized in larger amounts by plants, grasses, etc. in proportionally larger amounts relative to micronutrients. Nutrients include but are not limited to manganese, boron, copper, iron, chlorine, molybdenum, and zinc, potassium, nitrogen, calcium, magnesium phosphorus and sulfur, among others. The seed coating compositions can include various combinations and relative amounts of individual macronutrients.

D. Coating Techniques

Equipment utilized to for coating seeds with the disclosed seed coating compositions include, but are not limited to drum coaters, rotary coaters, tumbling drums, fluidized beds and spouted beds to name a few. The seeds can be coated via a batch or continuous coating process.

The seeds can be separated prior to coating which, in one embodiment, utilizes mechanical means such as a sieve. The separated seeds can then be introduced into a coating machine having a seed reservoir. In one embodiment, the seeds in the mixing bowl are combined with one or more of the coatings described herein and adhered with a binder or adhesive.

In one embodiment of the process, one or more layers as described herein can be added to coat the seed or agglomeration. Outer layers can be introduced sequentially to the rotating drum.

In another embodiment, agglomerators or agglomerator devices may also be utilized. Coating is performed within a rotary coater by placing seeds within a rotating chamber, which pushes the seeds against the inside wall of the chamber. Centrifugal forces and mixing bars placed inside the coater allow the seed to rotate and mix with a coating layer. Binder or other coating materials can be pumped into the proximate center of the coater onto an atomizer disk that rotates along with the coating chamber. Upon hitting the atomizer disk, liquid adhesive is then directed outward in small drops onto the seed.

In one embodiment, seed coating techniques include, for example, seed in a rotating pan or drum. Seed is then misted with water or other liquid and then gradually a fine inert powder, e.g., Diatomaceous earth, is added to the coating pan. Each misted seed becomes the center of a mass of powder, layers, or coatings that gradually increases in size. The mass is then rounded and smoothed by the tumbling action in the pan, similar to pebbles on the beach. The coating layers are compacted by compression from the weight of material in the pan. Binders often are incorporated near the end of the coating process to harden the outer layer of the mass. Binders can also reduce the amount of dust produced by the finished product in handling, shipping and sowing. Screening techniques, such as frequent hand screening, are often times utilized to eliminate blanks or doubles, and to ensure uniform size. For example, tolerance for seed coating compositions described herein can be about 1/64th inch (0.4 mm), which is the US seed trade standard for sizing.

In yet another embodiment, the seed coating compositions and methods described herein comprises "in situ coating". In situ coating means, in one embodiment, where a raw or non-coated seed is implanted in a hole, cavity or hollowed area in the ground and immediately or soon thereafter a coating composition is sprayed or applied directly into the hole, cavity or hollowed area to surround or partially surround the seed. Typically, the application of the seed as well as application of the coating composition are performed mechanically, but is understood that either or both of the referenced applications can be performed manually as well.

The coating can also be applied to a seed by spraying, dipping or brushing.

III. Methods for Providing Tolerance or Resistance to Abiotic Stress Conditions

Methods for providing seeds and plants with resistance or tolerance to abiotic stress conditions are provided. The methods include inoculating the seed or plant with an effective amount ($10^6$-$10^8$ bacteria/ml) of SA187 to provide the seed or plant with resistance to the abiotic stress conditions. The inoculation of the plant can be in the rhizosphere of the plant. The rhizosphere is the area around a plant root that is inhabited by a unique population of microorganisms. Alternatively, the plant root can be inoculated directly. In certain embodiments, the plant root is coated with SA187.

A method for providing a seed or plant with resistance to abiotic stress condition include coating the seed or a root of the plant with an effective amount of SA187 to provide the seed or plant with resistance or tolerance to abiotic stress conditions.

Yet another embodiment provides a method of improving growth of a seed or plant under abiotic stress conditions by growing the seed or plant in a plant substrate, wherein the plant substrate includes an effective amount of SA187 to colonize the seed or a root of the plant to provide abiotic stress resistance to the seed or plant.

Still another embodiment provides a method of improving tolerance of a seed or plant against abiotic stress conditions by growing the seed or plant in a plant substrate comprising an effective amount of SA187 to provide the seed or plant with tolerance to the abiotic stress conditions.

Yet another embodiment provides a method of providing a plant with abiotic stress resistance by inoculating the plant's rhizosphere with SA187.

One embodiment provides a method for increasing crop yield or crop biomass by inoculating fallow soil with SA187, planting crop seeds or crop seedlings into the inoculated fallow soil, cultivating the crop seeds or crop seedlings into mature plants, and harvesting the mature plants, wherein the harvested mature plants have increased crop yield or crop biomass or both relative to similar crop seeds or crop seedlings cultivated in soil without SA187.

Another embodiment provides a method for increasing crop yield or crop biomass by inoculating roots of crop plants with SA187 to increase crop yield or crop biomass or both relative to crop plants grown without SA187. The crop plants can be grown in a field, pasture, land, farmland, or in gardens.

Crops that can be treated with SA187 include but are not limited to alfalfa, cotton, wheat, maize, soybean, oat, barley, potato, and sugar beets.

EXAMPLES

Example 1: Identification of SA187

Methods

Organisms

*Enterobacter* sp. SA187 is endophytic bacteria isolated from surface sterilized root nodules formed on roots of pioneer plant *Indigofera argentea* Burm.f. (Fabaceae). Plants were collected from different regions in the Jizan area (16° 56.475' N, 42° 36.694' E) of Saudi Arabia. SA187 has been shown to possess plant growth promoting activities, such as the production of siderophores and indole acetic acid (IAA).

Sequencing

The genomic DNA of SA187 was extracted using the Qiagen's DNeasy blood and tissue kit following the manufacturer protocol. The DNA was then sequenced using paired-end Illumina MiSeq and the library preparation was constructed as described previously (1). Contig assembly was done with Spades assembler version 3.6 (4) with a 1 KB contig 52 cutoff size.

Total RNA was extracted from 5-day-old plants inoculated or not with SA187 and transferred for 10 more days on ½ MS plates with or without 100 mM NaCl using the Nucleospin RNA plant kit (Macherey-Nagel), including DNase treatment, and following manufacturer's recommendations.

RNA samples were used for Illumina HiSeq deep sequencing (Illumina HiSeq 2000, Illumina). Three biological replicates were processed for each sample. Paired-end sequencing of RNA-seq samples was performed using Illumina GAIIx with a read length of 100 bp. Reads were quality-controlled using FASTQC (http://www.bioinformatics.babraham.ac.uk/projects/fastqc/). Trimmomatic was used for quality trimming[8]. Parameters for read quality filtering were set as follows: Minimum length of 36 bp; Mean Phred quality score greater than 30; Leading and trailing bases removal with base quality below 3; Sliding window of 4:15. TopHat v2.0.9[9] was utilized for alignment of short reads to the *Arabidopsis thaliana* genome TAIR10 (Supplementary Table 1), Cufflinks v2.2.0[10] for transcript assembly and differential expression. To identify differentially expressed genes, specific parameters (p-value: 0.05; statistical correction: Benjamini Hochberg; FDR: 0.05) in cuffdiff were used. Post-processing and visualization of differential expression were done using cummeRbund v2.0.0". Gene is considered as regulated if fold change>log $2^{|0.6|}$ and q-value <0.05. Results were confirmed by analyzing 12 genes using qPCR method.

For qPCR analysis, plant RNAs were purified as described previously. For bacterium, SA187 incubated 4 h in ½MS or ½MS+100 mM, at 28° C., under the dark, were used for RNA extraction, using the RiboPure™ RNA Purification Kit, bacteria (Ambion) following manual instructions for Gram-(−) bacteria, with the exception that no beads were used during bacterial lysis. RNA extraction was followed by DNAseI treatment in order to obtain purified total RNA.

cDNAs were synthetized using SuperscriptIII (Invitrogen), 1 µg of total RNA and oligo-dT following manufacturer's recommendations. For *Arabidopsis* gnee expression analyses, ACTIN2 (At3g18780) and UBIQUITIN 10 (At4g05320) were used as reference genes. For SA187 gene expression analyses, infB, rpoB and gyrB were used as reference genes. All reactions were done in a CFX96 Touch™ Real-Time PCR Detection System (BIO-RAD) as follows: 50° C. for 2 min, 95° C. for 10 min; 40×[95° C. for 10 sec and 60° C. for 40 sec]; and a dissociation step to validate the PCR products. All reactions were performed in three biological replicates, and each reaction as a technical triplicate. Gene expression levels were calculated using Bio-Rad CFX manager software.

Hierarchical Clustering and Gene Family Enrichment

*Arabidopsis* regulated genes were used to generate HCL tree using Multi Experiment Viewer (MeV 4.9.0 version, TM4, https://sourceforge.net/projects/mev-tm4/files/mev-tm4/MeV %204.9.0/). Raw data were normalized for every gene and transformed in log 2. Hierarchical clustering was performed using Euclidian distances, average linkage and leaf order optimization. Heat colors indicate log 2 fold change.

Gene enrichment analyses were performed using AmiGO website (http://amigo1.geneontology.org/cgi-bin/amigo/term enrichment). Each cluster were analyzed using default parameter.

Results

De novo assembly of MiSeq reads for *Enterobacter* sp. SA187 resulted in 14 contigs with a total length of 4,404,403 bp and a mean contig size of 314,600 bp. The N50 was 2,296,004 bp and the L50 has been reached in 1 contig. The GC content of this draft genome was 56%. Megablast (5) comparison of the SA187 concatenated contigs against the NCBI reference genome database (http://www.ncbi.nlm.nih.gov/genome/) revealed the 57 closest relative genomes being *Enterobacter sacchari* SP1 with a coverage of 63% and sequence identity of 95% (Accession number NZ_CP007215.2) (6). The annotation of *Enterobacter* sp. SA187 was carried out using the default INDIGO pipeline (7) with the exception of open reading frame (ORFs) prediction by FragGeneScan (8). The annotation of SA187 resulted in 3,087 ORFs, 9 rRNA, 75 tRNA, and 145 ncRNA.

The annotation predicted a number of siderophore pathway genes such as entE, entC, entA, entB, entF, as well as entS, an MFS transporter of enterobactin. An ABC transporter involved in iron uptake, sitABCD, was also found, as well as five copies of the iron complex outer membrane receptor (fhuA) and a TonB-dependent outer membrane iron-enterobactin/colicin (fepA). Generally, PGPR bacteria enhance plant growth through the synthesis of IAA from tryptophan via indole pyruvate as the main pathway (9). The SA187 genome harbors a number of genes involved in this pathway, but lacks the gene encoding for indolepyruvate decarboxylase (ipdC). Moreover, the SA187 genome codes for the enzyme tryptophanase (TnaA) (EC: 4.1.99.1), which can transform tryptophane into indole.

Example 2: Nucleotide Sequence Accession Numbers

Genome of *Enterobacter* sp. SA187 was deposited at DBFEMBL/GenBank under accession number MORB00000000 (which is incorporated herein in its entirety. The genome of SA187 contains SEQ ID NO:1-13.

Results

Based on 16S rDNA sequencing and comparison, SA187 was suggested to belong to the *Enterobacter* genus, with high homology with *Enterobacter kobei* strains.

The 16S ribosomal RNA gene sequence (or 16S rRNA) is deposited at DDBFEMBL/GenBank under the accession no KY194757.

Based on the 16S rRNA gene sequence the SA187 is closely related to *Enterobacter* kobei CCUG 49023$^T$ and *Enterobacter aerogenes* strain KCTC 2190 with 99% sequence similarity. One embodiment provides a bacterium comprising SEQ ID NO:1, 2, 3, 4, 5, 6, 7, 8, 9, 10, 11, 12, 13, 14, or a combination thereof.

Example 3: Salt Tolerance on *Arabidopsis thaliana*

Materials and Methods

SA187 was first tested in vitro on *Arabidopsis thaliana* plants. *Arabidopsis thaliana* Columbia-0 ecotype have been germinated on ½ strength MS medium plates, a generic synthetic plant growth medium (adapted from Murashige and Skoog, 1962), containing $10^7$ bacterial cells per plate, control plants were grown on regular ½ MS plates. After 5 days of germination, seedlings were transferred on 2 different medium: ½ MS (control condition), ½ MS+100 mM NaCl (Salt condition).

*Arabidopsis thaliana* Columbia-0 seeds were surface sterilized 10 min in 70% EtOH+0.05% Sodium Dodecyl Sulfate on a shaker, washed 2 times in 96% EtOH and let to dry. Sterilized seeds were sawn on ½ MS plates (Murashige and Skoog basal salts, Sigma) containing $2 \cdot 10^5$ cfu·mL$^{-1}$ (+SA187), stratified for 2 days at 4° C. in the dark and then placed vertically for germination during 5 days. Calculated amount of bacterial suspension was added to pre-cooled agar medium during plate preparation.

Germination was considered as occurring when a radicle was detectable under the stereomicroscope. Average length of root hairs was determined based on images of 5 day-old roots (1 image per root at constant distance from the root tip, 25 seedlings per condition) captured using a Nikon AZ100M microscope equipped with an AZ Plan Apo 2× objective and a DS-Ri1 camera (Nikon). All root hairs in focus were measured in ImageJ (https://imagej.nih.gov/ij/), average value and standard deviation were calculated from 10% longest root hairs to eliminate non-developed root hairs and describe the maximal elongation capacity of root hairs.

Figure 4A:
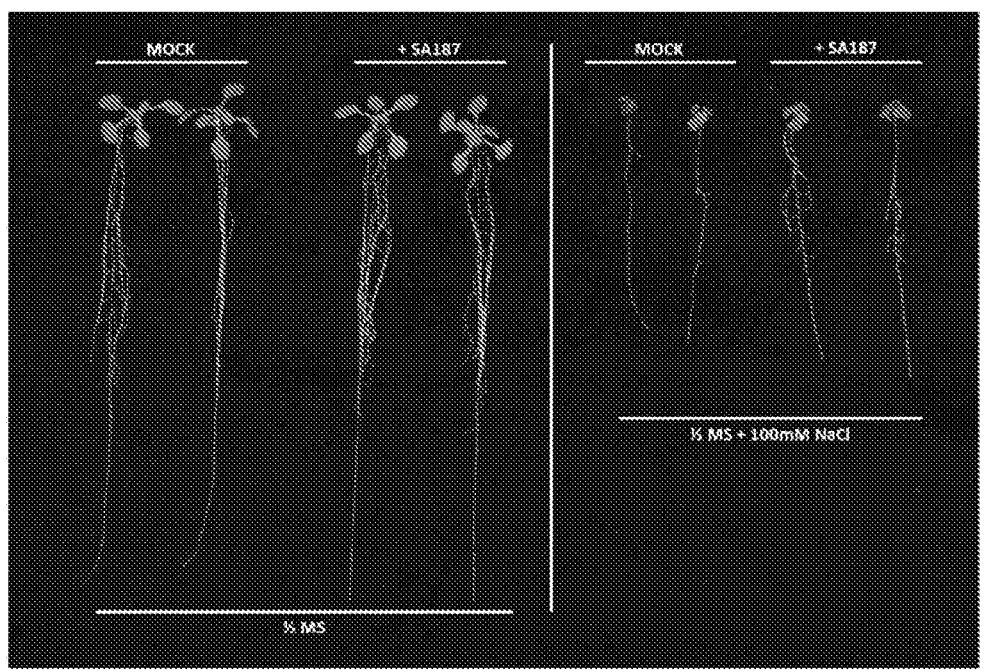
FIG. 4A is a photograph of germinating *Arabidopsis thalia* seeds grown on ½ MS containing $10^7$ bacteria per plate (left panel) with (+SA187) or without (−SA187). Five day old seedlings were then transferred to ½ MS+/−100 mM NaCl plates (right panel). Photographs were taken after 10 days of treatment.
Figure 4B:
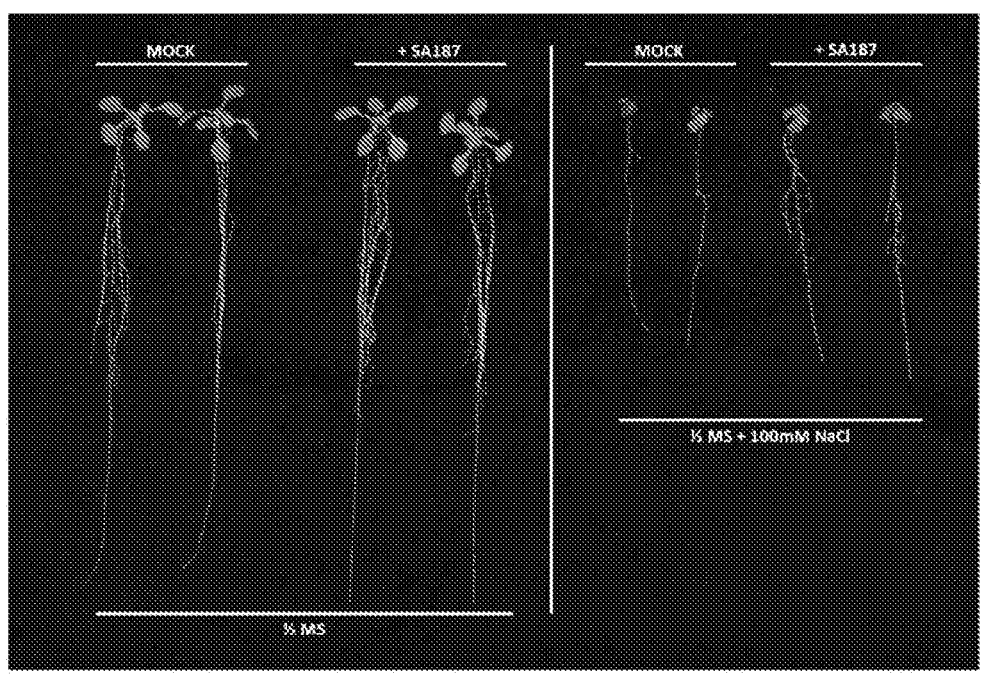
FIG. 4B is a photograph of germinating *Arabidopsis thalia* seeds grown on ½ MS containing $10^7$ bacteria per plate (left panel) with (+SA187) or without (−SA187). Five day old seedlings were then transferred to ½ MS+/−100 mM NaCl plates (right panel). Photographs were taken after 20 days of treatment.

Five-day-old seedlings were transferred on ½ MS plates with or without 100 mM NaCl (Sigma). Primary root length was measured using ImageJ software after scanning the plates. Lateral root density was evaluated as detectable number of lateral roots under a stereo microscope divided by the primary root length (FIGS. 4A-4B). Fresh weight was measured 12 days after transfer of seedlings. Dry weight was measured by drying the different plant organs 2 days at 70° C. To address the ethylene involvement on *Arabidopsis* adaptation to salt stress, ACC (1-aminocyclopropane-1-carboxylic acid, Sigma), KMBA (2-keto-4-methylbutyric acid, Sigma), AVG (Aminoethoxyvinylglycine, Sigma) and AgNO$_3$ (Silver nitrate, Sigma) were added concentrations in ½ MS plates with 100 mM NaCl.

For osmotic shock treatment, stress evaluation was performed by transferring plants on PEG plates (−0.5 MPa) as described previously[4]. For the heat stress treatment, 6-day-old seedlings plants were given a 37° C. preheat treatment for 1 h, and then subjected to heat stress of 42° C. for 3 h. Plants were then transferred to normal growth conditions (22° C.) for one week. The survival rate was quantified by counting the percentage of the surviving plants. All plants were grown in long day conditions in growth chambers (Percival; 16 h light/8 h dark, 22° C.) for 10 to 12 more days. Each experiment was performed at least in three biological replicates.

Na$^+$ and K$^+$ Content Determination

Dry rosettes and root systems were weighted. All samples were measured individually except for salt-treated root systems, whereby pools of 3 samples were used for measurements. Sodium and potassium concentrations were measured for shoot and root dry samples by digestion method, using 1 mL of freshly prepared 1% HNO$_3$ (trace metal grade, Fisher Scientific) that was added to the pre-weighed samples. The concentrations of sodium and potassium were determined, using Inductively Coupled Plasma Optical Emission Spectrometer (Varian 720-ES ICP OES, Australia).

Results

Figure 2A:
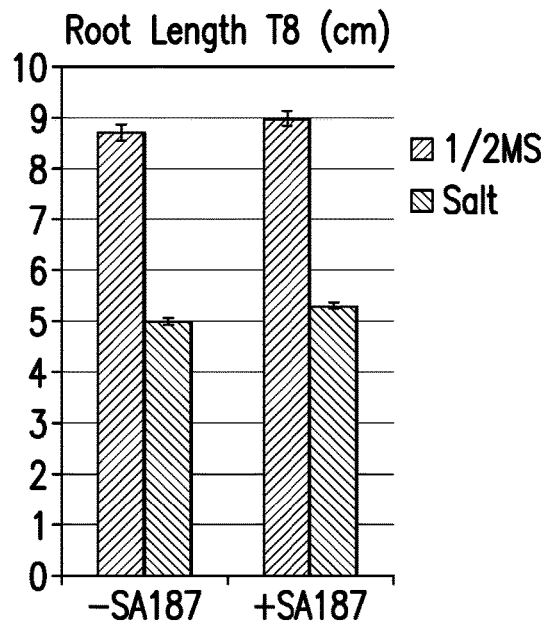
FIG. 2A is a bar graph of root length (cm) for 13 day old *Arabidopsis* seedlings treated for 8 days with ½ MS (control condition; left column) and 100 mM NaCl (salt condition; right column) for plants inoculated with (+SA187) and plants without (−SA187).
Figure 2B:
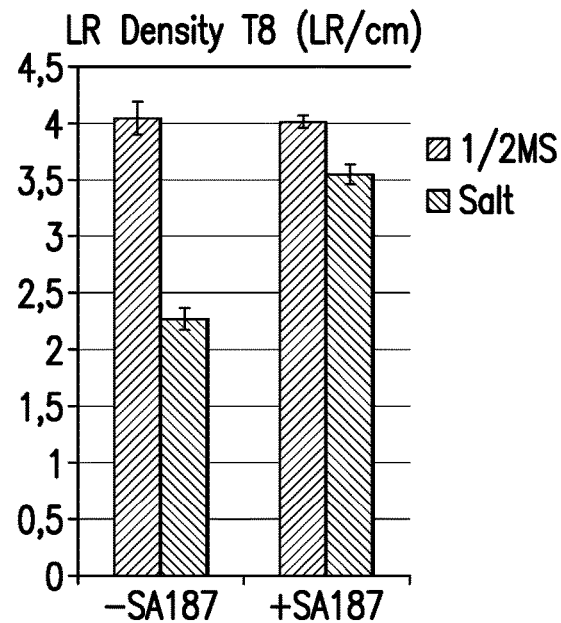
FIG. 2B is a bar graph of lateral root density (cm) for 13 day old *Arabidopsis* seedlings treated for 8 days with ½ MS (control condition; left column) and 100 mM NaCl (salt condition; right column) for plants inoculated with (+SA187) and plants without (−SA187).
Figure 3:
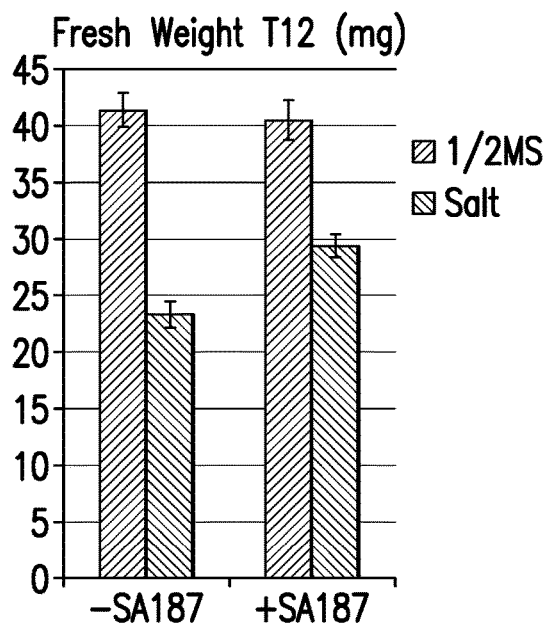
FIG. 3 is a bar graph showing the fresh weight (mg) of 17 day old *Arabidopsis* seedlings treated for 12 days with ½ MS (control condition, left column) and 100 mM NaCl (salt condition, right column) for plants inoculated with (+SA187) and plants without (−SA187).

Root length, lateral root density were assayed after 8 days (FIG. 2). After 12 days of treatment, plants were weighed (FIG. 3). Overall those results indicate that SA187 can enhance *Arabidopsis* growth under salt stress conditions by ca. 25% fresh weight and increasing the lateral root density of the stressed plants by 60%. As shown in FIG. 3, this increase will be amplified over time indicating that this beneficial action will increase over time ending with highly improved plant growth when faced by salt stress.

Similar results were obtained using ½ MS+5% PEG (PolyEthylene Glycol 6000), a compound known to induce osmotic stress on the plants.

Figure 5:
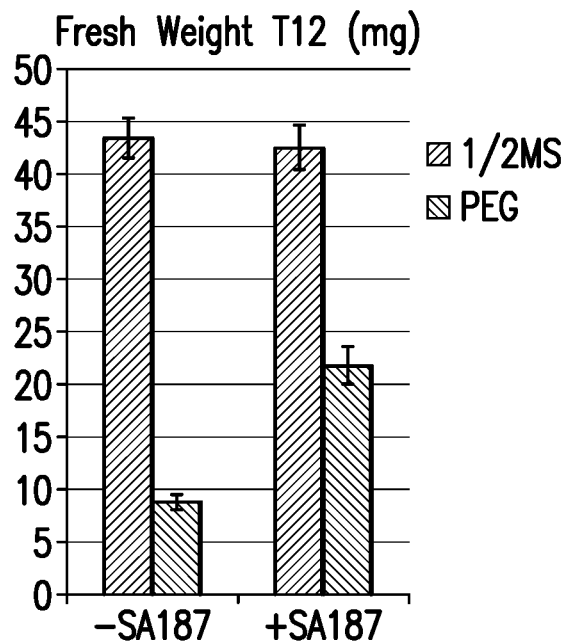
FIG. 5 is a bar graph of fresh weight (mg) of 17 day old *Arabidopsis* seedlings treated for 12 days with ½ MS (control, left column) and 5% PEG (drought mimicking condition, right column) treated with (+SA187) or without (−SA187) SA187.

SA187 possess a number of plant growth promoting (PGP) traits, such as the solublization of Zn, production of siderophores and production of indole acetic acid (IAA). SA187 can tolerate different abiotic stresses including salt stress up to 2M NaCL and osmatic stress-up to 20% poly ethylene glycol 8000: PEG8000) mimicking drought stress in vitro (FIG. 5).

Those results show that SA187 induces tolerance to multiple environmental stresses on *Arabidopsis thaliana*. It is also important to note that SA187 does not have any detrimental effect on plant growth under optimal conditions.

Example 4: Drought Tolerance Test on *Arabidopsis thaliana*

Materials and Methods

The beneficial effect of SA187 was also tested in a greenhouse: Bacterialized 3 week old *Arabidopsis* plants were submitted to a 3 week drought treatment and then rewatered again. After one week of rewatering, aerial parts were collected and weighed.

Results

Figure 6:
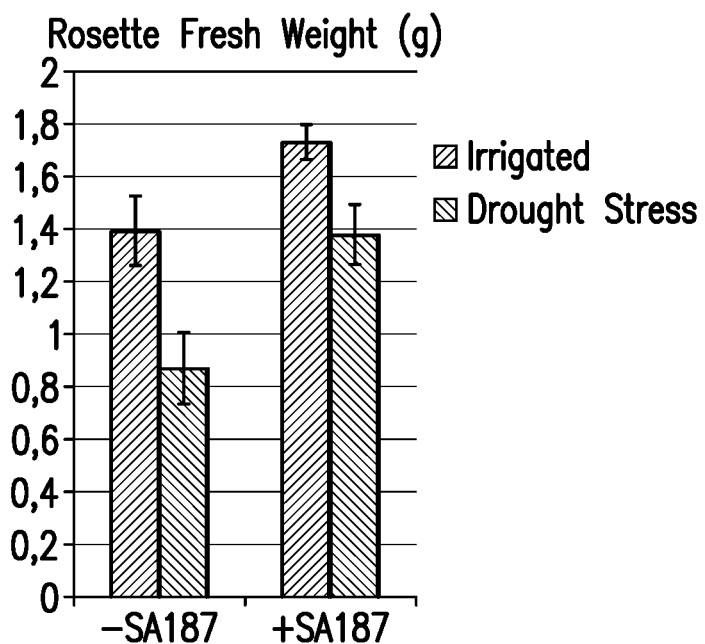
FIG. 6 is a bar graph of rosette fresh weight (g) of *Arabidopsis* plants submitted to a 3 week drought treatment as in FIG. 5 with (+SA187) or without (−SA187).

As shown in FIG. 6, SA187 increases *Arabidopsis* fresh weight by 25% in optimal conditions and almost 60% after water stress confirming the results obtained in vitro. This experiment also points out that SA187 acts beneficially in the long term on the development of *Arabidopsis thaliana* in normal conditions.

Example 5: Field Trial on Durum Wheat

Materials and Methods

SA187 was tested during a field trial at the ICBA station in Dubai (United Arab Emirates). These assays aimed to verify if the results obtained in highly controlled conditions could be confirmed in field conditions. Seed lots of durum wheat were inoculated by soaking in a bacterial solution and kept shaking for 4 hours, then allowed to dry on filter paper. Seed sowing was performed on the fields of the ICBA experimental station. Soil samples were collected from the plots irrigated with fresh water for analysis. The average value for the pH was 7.45 and the salinity of the soil was EC=4.9 ds/m (EC>4 ds/m is considered saline). Germination was recorded in all plots without any visible differences between subplots.

Field Trial

Two field stations were chosen to conduct the trail experiments; both fields are located in desert area exposed to high average temperature through the year, low rain, availability of source of ground water, poor loamy sandy soil, with poor organic matter. Unless mentioned later, other agronomic practices were kept uniform across the treatments throughout the experiment in the two field station.

Seeds of durum wheat (*Triticum durum*) local Karim variety were washed thoroughly in sterile distilled water and then soaked in bacterial suspension solution ($2.10^8$ cell·mL$^-$ $_1$) for 4 h with shaking, bacterial suspension was removed and the seeds left to air dry over 3 mM filter paper (Whatman) for 6 h. Durum wheat field trail was carried out at the SCADA field station at International Center for Biosaline Agriculture, Dubai, United Arab Emirates (ICBA-UAE), in period of 2014-2016 (N 25°5'40.9", E 55°23'23.6"). The experiment was conducted using a randomized complete block design; each plot is (2.5×2.0 m) with three replicates. Ten-row plots were prepared with intra- and inter row distances of 20 cm and 50 cm, respectively. All the plots were irrigated with ground water with EC=0.3 dS·m$^{-1}$, the average soil pH was 7.45 and soil salinity EC=4.9 dS·m$^{-1}$. The agronomical data were collected on plant height, plant biomass, number of tillers per plant, spike height, number of spikes plant, number of seeds per spike, and total grain yield per plot.

For inoculation of alfalfa which has smaller seeds size, a slurry was prepared consisting of sterilized peat, a broth culture of SA187, and sterilized sugar solution (10%) in the ratio 5:4:1 (w/v/v). Subsequently, alfalfa seeds were coated with the slurry at a rate of 50 mL·kg$^{-1}$. For the control, seeds were coated with a similar mixture without bacteria. Field trial was conducted at experimental station in Hada Al-Sham, Kingdom of Saudi Arabia, in the period of 2015-2016 (N 21°47'47.1" E 39°43'48.8"). The experiment was a randomized complete block design with a split-split plot arrangement of four replicates, plots (2×1.5 m) with seed spacing 20 cm row-to-row. The field was irrigated using saline ground water with three different salinity level (EC 3.12, 5.46, and 7.81 dS m$^{-1}$), at the research station, two sources of water were available with a salinity of EC 3.12 and 7.81 dS m$^{-1}$, and saline water with EC 5.46 dS m$^{-1}$ was prepared by mixing the two sources. The average soil pH was 7.74 and soil salinity EC=1.95 dS m$^{-1}$. The agronomical data were recorded every 25-30 days after each cut; this includes plant height and yield as fresh and dry weight.

Results

Figure 7A:
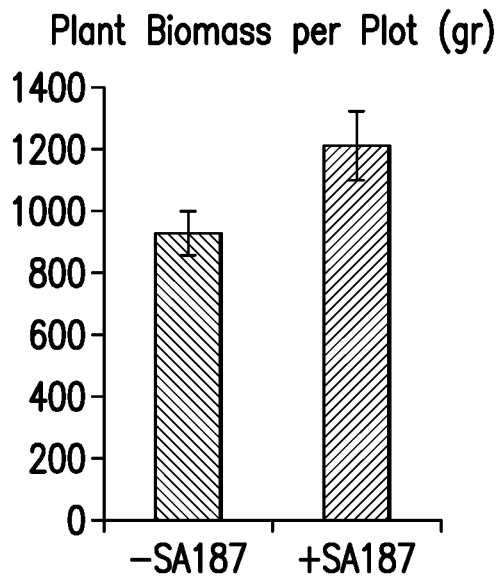
FIG. 7A is a bar graph of plant biomass per plot (gr) of Durum wheat inoculated with (+SA187) or without (−SA187).
Figure 7B:
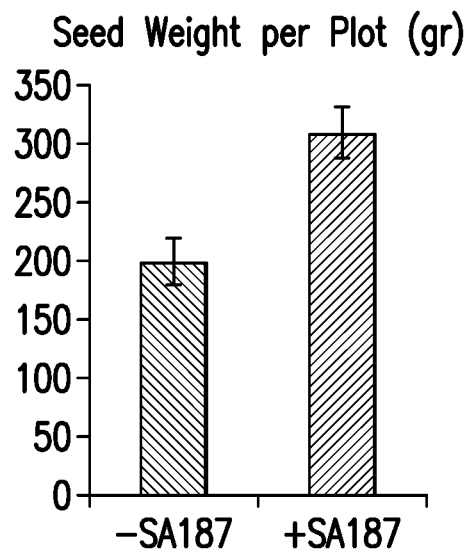
FIG. 7B is a bar graph of seed weight per plot (gr) of Durum wheat inoculated with (+SA187) or without (−SA187).
Figure 7C:
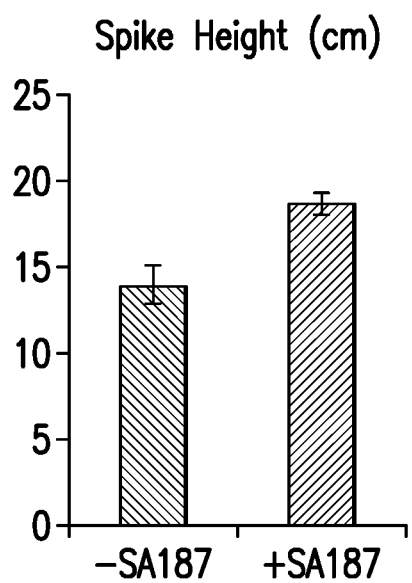
FIG. 7C is a bar graph of spike height (cm) of Durum wheat inoculated with (+SA187) or without (−SA187).
Figure 7D:
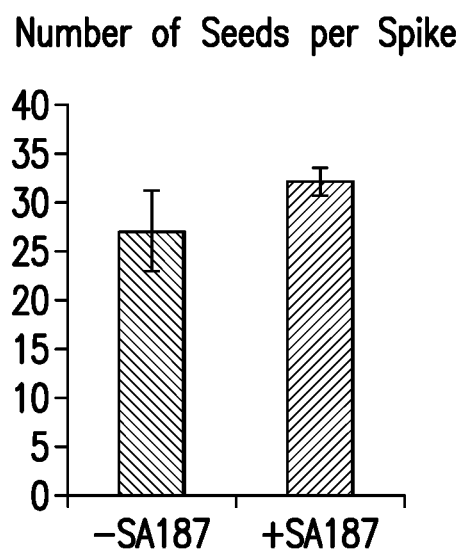
FIG. 7D is a bar graph of number of seeds per spike of Durum wheat inoculated with (+SA187) or without (−SA187) *Enterobacter endophyticus* sp. nov.

Overall this field experiment proved that SA187 increased crop yield by 50% in the hot and arid conditions of fields in the United Arab Emirates showing increased plant biomass (FIG. 7A), seed number per spikes (FIG. 7D). and seed weight per plot (FIG. 7B). These results establish that SA187 can be used for agronomical purposes as it can significantly enhance crop yield.

All together, the results show the beneficial impact of SA187 on plant growth and yield. This bacterial strain is performing positively on different plant species and improves their development and yield under environmental stresses in controlled in vitro and greenhouse conditions but also in open field trials showing its wide potential for agronomical application.

Example 6: Assessment of Stress Tolerance

To test whether SA187 can confer enhanced stress tolerance to plants beyond its natural host, the model crucifer plant *Arabidopsis thaliana* was tested. SA187 did not negatively influence the germination rate of *Arabidopsis* seeds, and morphological changes became obvious 5 days after germination: Primary roots were significantly shorter and exhibited longer root hairs compared to non-treated seedlings.

Materials and Methods

SA187 inoculated plants were transferred on medium with or without 100 mM NaCl to monitor PGP or stress-tolerance promoting (STP) capacity.

Results

Figure 8A:
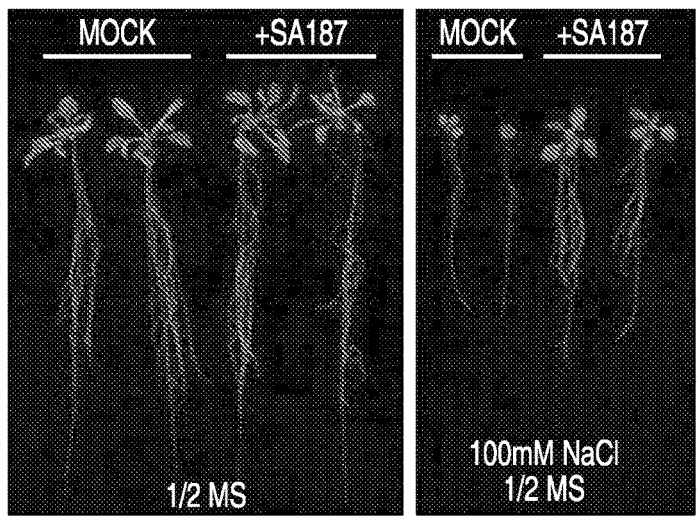
FIG. 8A is a photograph of SA187-colonized 25-day-old *Arabidopsis* plants showing enhanced growth under salt stress.
Figure 8B:
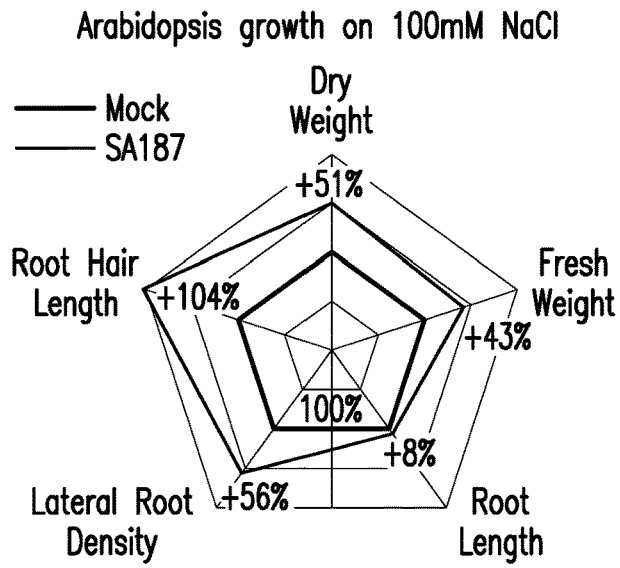
FIGS. 8B and 8D are graphs showing growth parameters of 17-day-old SA187-colonized seedlings exposed to salt stress (½ MS+100 mM NaCl) or osmotic stress (−0.5 MPa) (FIG. 8D). Root hair length was measured on 5-day-old seedlings.
Figure 8C:
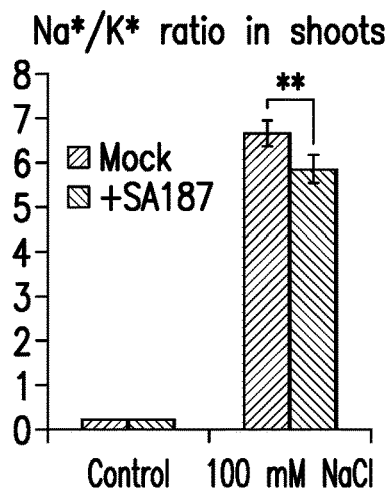
FIG. 8C is a bar graph of shoot Na+/K+ratio of SA187-colonized seedlings exposed to salt stress for 12 days.
Figure 8D:
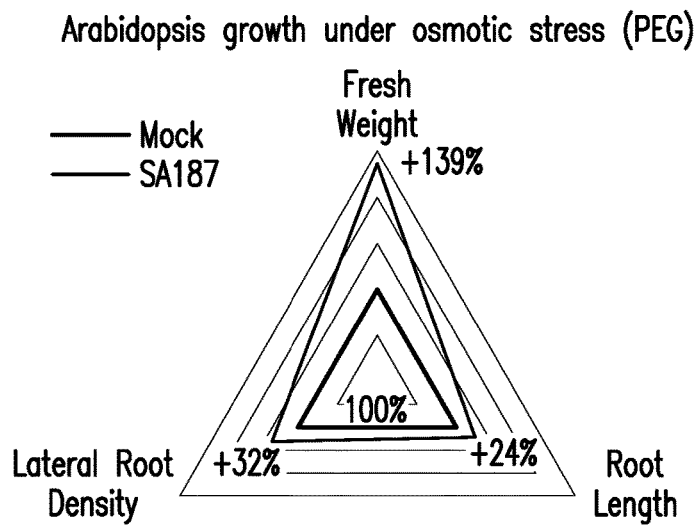

As evaluated by shoot and root fresh and dry weight, root length, lateral root density or ion content, SA187 had a neutral impact on *Arabidopsis* growth in control conditions, indicating that SA187 is not PGPR per se. However, under salt-stress condition, SA187-treated plants exhibited clear positive effects as shown by an increased fresh weight of roots and shoots (FIG. 8A, 8B, 9A-9C). Principal root growth was similar between control and SA187-inoculated plants under salt stress conditions, but lateral root density was significantly increased (FIG. 8B). The higher salt tolerance of SA187-inoculated plants can be explained by an enhanced K$^+$ content, thereby changing the Na$^+$/K$^+$ ratio under salt stress conditions.

Figure 8E:
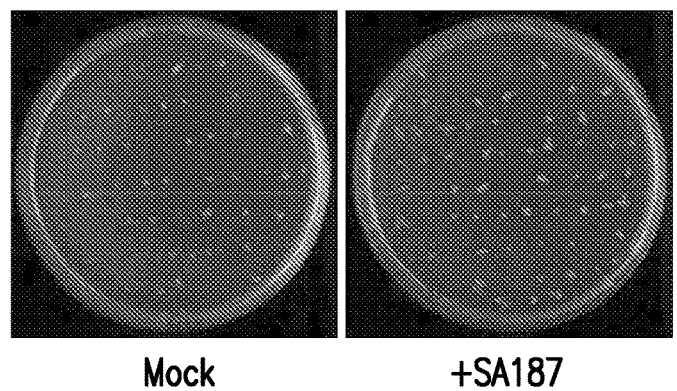
FIG. 8E is a photograph showing increased survival into heat stress in *Arabidopsis* inoculated with SA187.
Figure 8F:
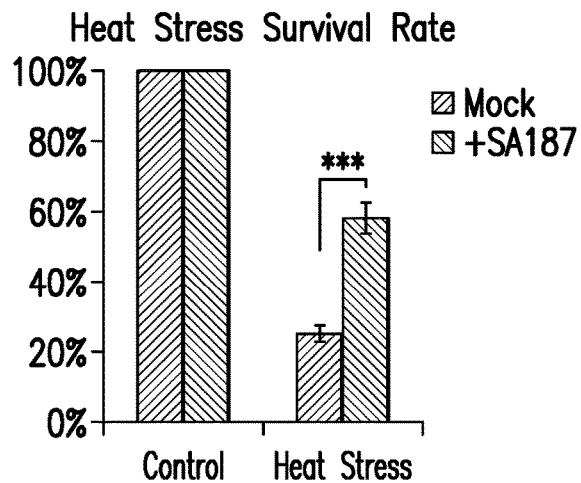
Figure 8G:
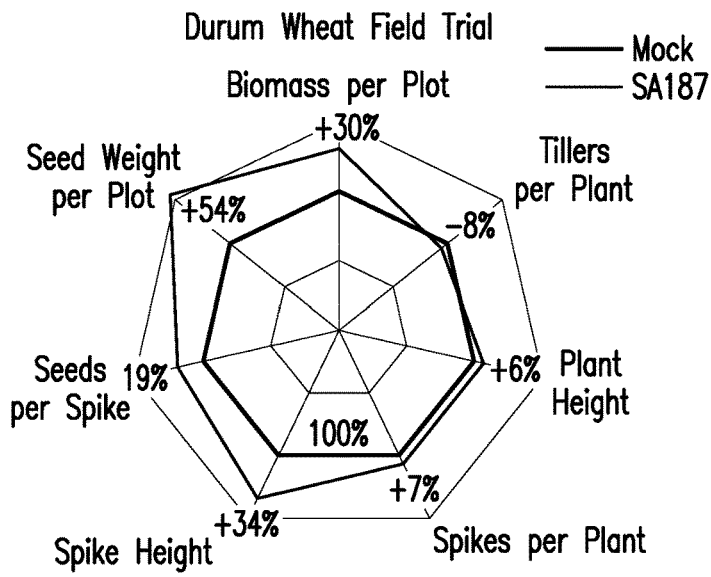
FIG. 8G is a graph of growth parameters of SA187-colonized 140-day-old field-grown durum wheat plants.
Figure 8H:
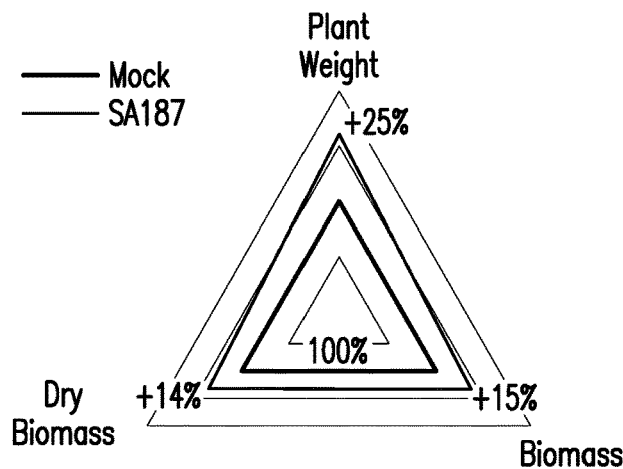

SA187 was also evaluated for its capacity to enhance *Arabidopsis* tolerance to other abiotic stresses. SA187-inoculated plants exhibited a higher heat stress survival rate (52%) when compared to non-treated plants (22%) (FIG. 8G, 8H). Plant growth was also improved by SA187 when subjecting plants to osmotic stress (FIG. 8). These results indicate that SA187 confers multi-stress tolerance to *Arabidopsis thaliana*.

Example 7: Assessment of Agronomic Use of SA187

Materials and Methods

To evaluate the potential agronomic use of SA187, its beneficial activity was tested under desert field conditions using two agronomically important crops: A durum wheat field trial was performed in poor sandy soil in the hot desert climate of Dubai, United Arab Emirates.

Results

Figure 8I:
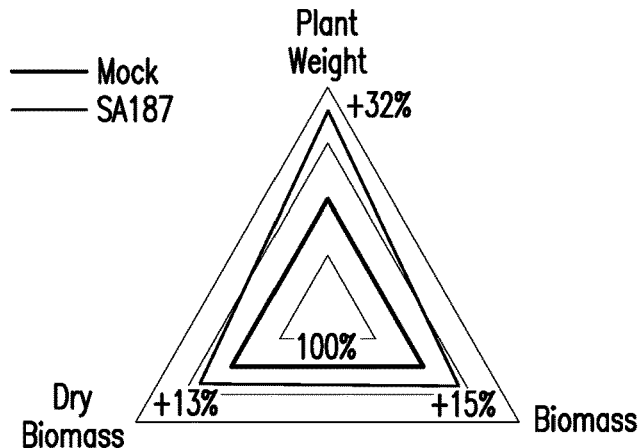
Figure 9A:
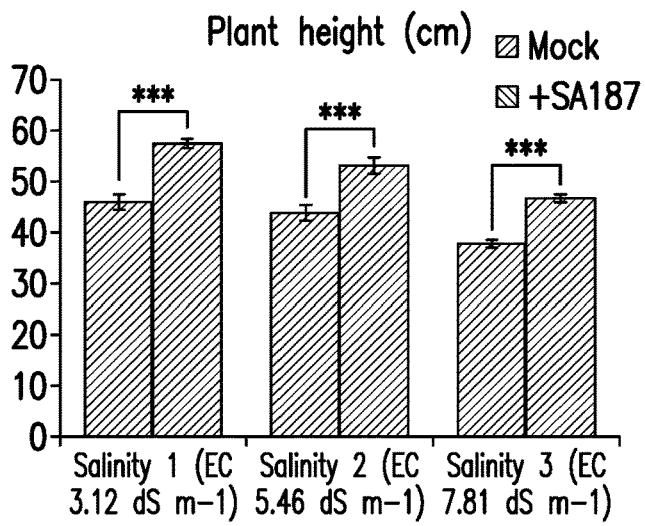
FIG. 9A is a bar graph of plant height under salinity conditions when treated with SA187.
Figure 9B:
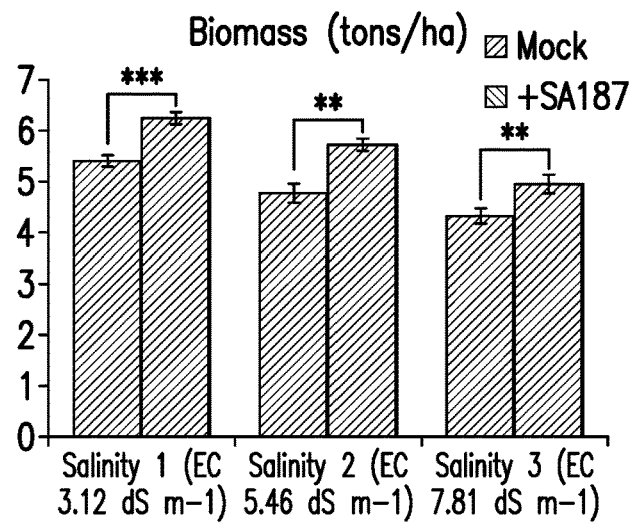
FIG. 9B is a bar graph of biomass of plants treated with SA187 and cultured under salinity conditions.
Figure 9C:
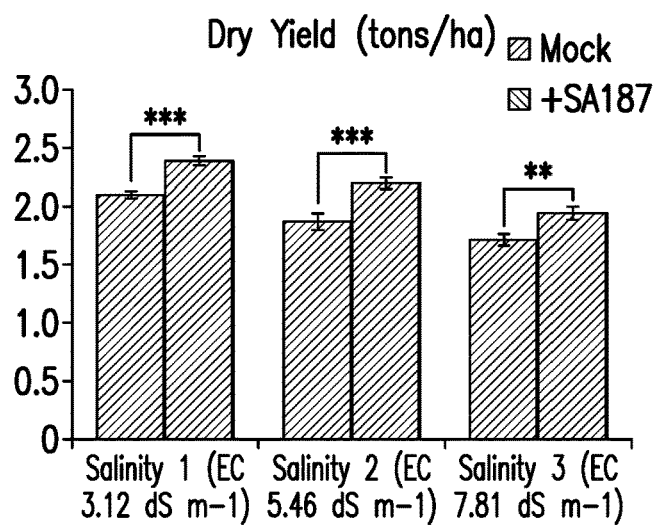
FIG. 9C is bar graph of dry yield of plants treated with SA187 and cultured under salinity conditions.

During a typical growing season, SA187 enhanced wheat biomass by 30%, but also spike height, and most importantly grain yield by over 50% (FIG. 8I). Alfalfa was grown on sandy soil fields near Jeddah, in Saudi Arabia. SA187-treated alfalfa exhibited an increase of around 20% for plant height and biomass, independently of irrigation, with regular or high salty water (FIG. 8E).

Example 8: Assessment of Plant Interaction with SA187

Materials and Methods

To characterize the interaction of SA187 with plants in more detail, its capacity to colonize *Arabidopsis* seedlings was analyzed on ½ MS agar or turf-based soil.

Generation of GFP-Labelled Bacteria

SA187 was genetically labeled with the GFP expressing cassette by taking advantage of the mini-Tn7 transposon system[5]. In order to specifically select for the bacterium carrying the GFP integration in the genome, a spontaneous rifampicin resistant version of the strain was obtained first[6]: an overnight-grown culture of SA187 was plated on LB plates amended with 100 µg·ml$^{-1}$ of rifampicin and the plates were incubated for 24 h at 30° C. At least 10 colonies, representing spontaneous rifampicin resistant mutants of the strain were streaked twice on LB plates containing 100 µg·ml$^{-1}$ of rifampicin and thereafter twice on LB plates supplemented with 200 µg·ml$^{-1}$ of rifampicin. The rif$^R$ SA187 strain was then used for the transformation assay by conjugation as described previously.

Results

SA187, which was stably transformed to express green fluorescent protein (GFP) while having the same effect on plant as the wild type strain colonized both roots and shoots (data not shown). On roots, colonies established themselves preferentially in grooves between epidermal cell files, before forming large colonies proportionally to the age of the root region. On vertical agar plates, SA187-GFP colonies were found inside root tissues in 22% of cases around the base of lateral roots (data not shown). Occasionally, SA187 was detected in the root apoplast of soil-grown seedlings far from lateral roots (data not shown). Bacterial colonies were also found deep inside the apoplast of hypocotyls, cotyledons and leaves, and in several cases bacterial cells were observed to penetrate through stomata of these organs (data not shown).

Example 9: Assessment of Signaling Pathways Affected by SA187

Materials and Methods

Figure 10A:
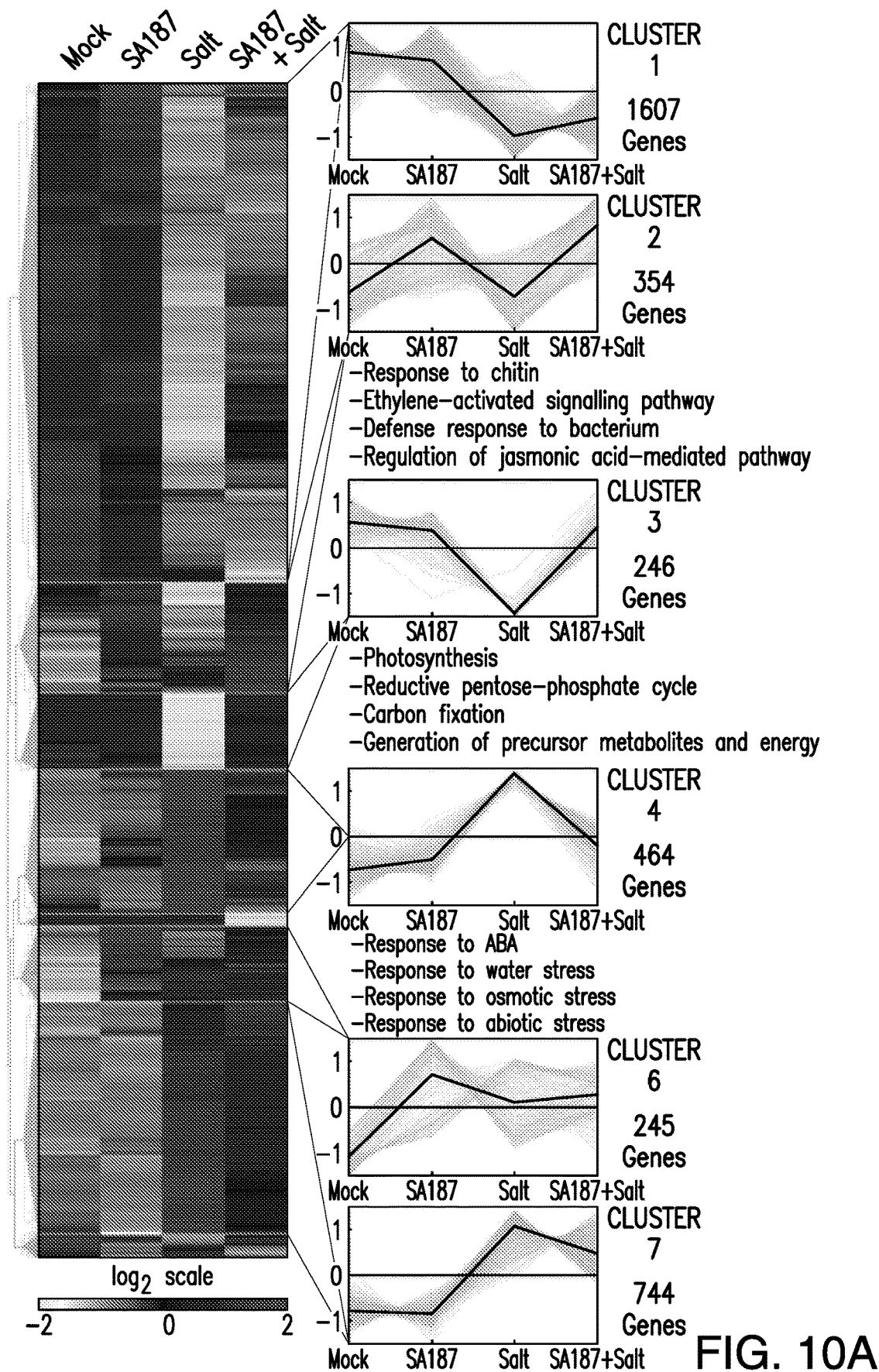
FIG. 10A is a hierarchical clustering (Euclidian distances) of deregulated genes in response to SA187, salt or both.

To identify which signaling pathways are affected in plants upon SA187-colonization under normal and salt stress conditions, RNA-seq analyses were conducted, comparing 4 conditions: Mock treated plants (Mock), SA187-inoculated plants (SA187), salt treated (Salt) and SA187-inoculated plant under salt stress (SA187+Salt) (Extended Data Table 1). The transcriptome data were analyzed by hierarchical clustering into 8 groups (FIG. 10A).

Results

The major differences between SA187- and non-inoculated plants were observed in clusters 2, 3 and 4. Cluster 3 corresponds to genes with a role in primary metabolism, such as photosynthesis and energy metabolism, that are downregulated under salt stress conditions in non-inoculated plants, whereas cluster 4 genes are involved in ABA and abiotic stress, that are found to be upregulated in salt treated plants, but not when they are treated with SA187. These results indicate that under salt stress conditions, SA187 might maintain a high metabolic rate and not activate all of the abiotic stress response pathways. Cluster 2 represents defense related genes and in particular those for ethylene, jasmonic acid and chitin signaling. Interestingly, this cluster of genes is already upregulated when plants are inoculated by SA187 under non-salt conditions.

Figure 10B:
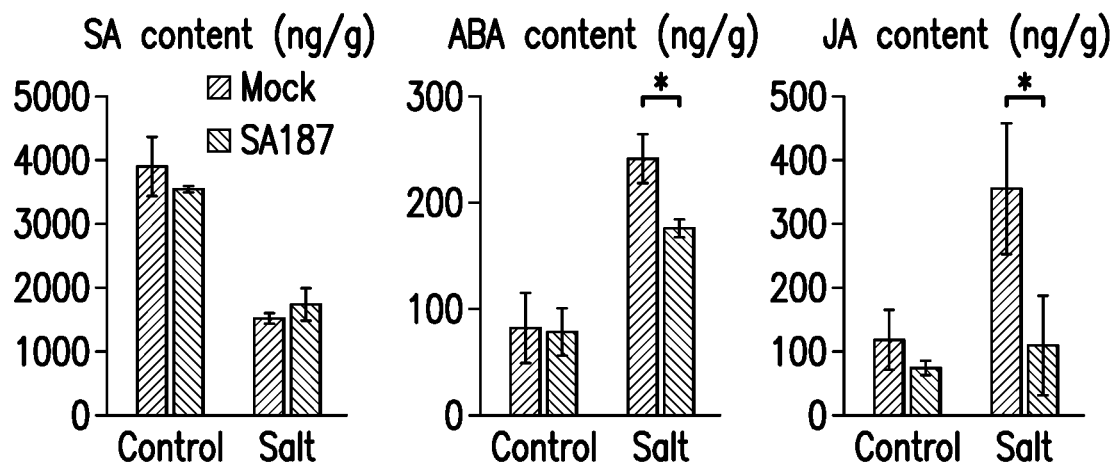
FIG. 10B are bar graphs of Salicylic acid (SA), abscisic acid (ABA) and jasmonic acid (JA) content of SA187-colonized or mock-treated plants after growth on ½ MS+/−100 mM NaCl for 12 days.

Since the transcriptome analysis indicated possible roles of the hormone pathways involved in abiotic and biotic stress, we measured SA, JA and ABA levels in control and colonized *Arabidopsis* plants. SA quantification showed that SA187 did not significantly change salicylate in the absence or presence of salt (FIG. 10B). ABA and JA levels in the absence of salt stress remained unchanged upon SA187 colonization, but their accumulation was significantly lower in SA187-colonized plants under salt stress (FIG. 10B). These data largely confirmed the transcriptome data and show that JA and to a lesser extent ABA levels are modulated by SA187 in salt stressed plants.

Example 10: Phytohormore Quantification

Materials and Methods

To complement the phytohormone quantification, hormone-deficient or insensitive mutants were analyzed. The beneficial activity of SA187 was evaluated on the JA-receptor coil-1 mutant[15] and JA-insensitivejar1[16], the ABA biosynthesis aba2 mutant[17] or the ABA receptor quadruple pyr1pil1pil2pil4 mutant (quad pyr)[18].

Hormone Content Analysis

For each sample, 10 mg of freeze-dried powder were extracted with 0.8 mL of acetone/water/acetic acid (80/19/1 v:v:v). For each sample, 2 ng of each standard was added to the sample: ABA, salicylic acid, jasmonic acid, and indole-3-acetic acid stable labelled isotopes used as internal standards were prepared as described previously[12]. The extract was vigorously shaken for 1 min, sonicated for 1 min at 25 Hz, shaken for 10 minutes at 4° C. in a Thermomixer (Eppendorf), and then centrifuged (8000 g, 4° C., 10 min). The supernatants were collected, and the pellets were re-extracted twice with 0.4 mL of the same extraction solution, then vigorously shaken (1 min) and sonicated (1 min; 25 Hz). After the centrifugations, three supernatants were pooled and dried.

Each dry extract was dissolved in 140 µL of acetonitrile/water (50/50; v/v), filtered, and analyzed using a Waters Acquity ultra performance liquid chromatograph coupled to a Waters Xevo Triple quadrupole mass spectrometer TQS (UPLC-ESI-MS/MS). The compounds were separated on a reverse-phase column (Uptisphere C18 UP3HDO, 100×2.1 mm, 3 µm particle size; Interchim, France) using a flow rate of 0.4 mL·min$^{-1}$ and a binary gradient: (A) acetic acid 0.1% in water (v/v) and (B) acetonitrile with 0.1% acetic acid. For ABA, salicylic acid, jasmonic acid, the following binary gradients were used (time, % A): (0 min, 98%), (3 min, 70%), (7.5 min, 50%), (8.5 min, 5%), (9.6 min, 0%), (13.2 min, 98%), (15.7 min, 98%), and the column temperature was 40° C. Mass spectrometry was conducted in electrospray and Multiple Reaction Monitoring scanning mode (MRM mode), in the negative ion mode. Relevant instrumental parameters were set as follows: capillary 1.5 kV (negative mode), source block and desolvation gas temperatures 130° C. and 500° C., respectively. Nitrogen was used to assist the cone and desolvation (150 $L \cdot h^{-1}$ and 800 $L \cdot h^{-1}$, respectively), argon was used as the collision gas at a flow of 0.18 $mL \cdot min^{-1}$. Samples were reconstituted in 140 μL of 50/50 acetonitrile/$H_2O$ (v/v) per mL of injected volume. The limit of detection (LOD) and limit of quantification (LOQ) were extrapolated for each hormone from calibration curves and samples using Quantify module of MassLynx software, version 4.1.

Results

Figure 10C:
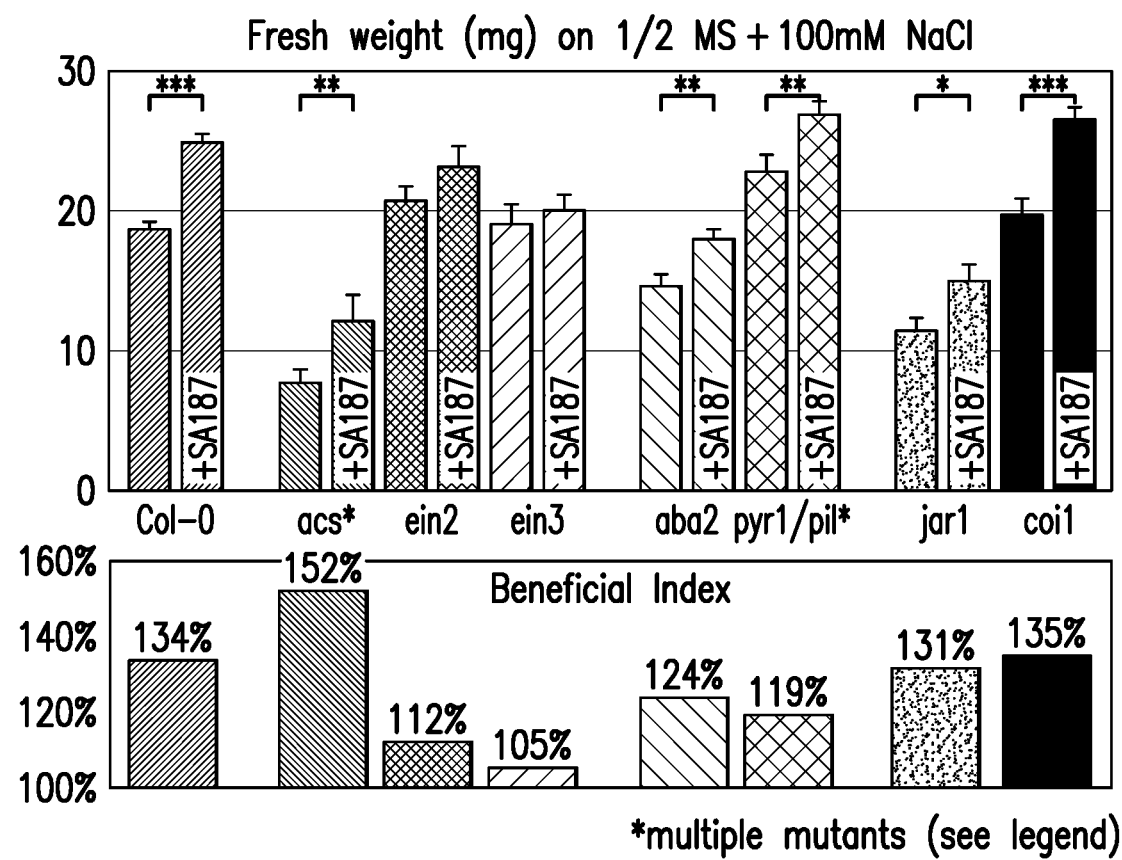
FIG. 10C are bar graphs of fresh weight and beneficial index of SA187-treated mutants in hormonal pathways under salt stress during 12 days.

In all cases, SA187 beneficial activity was maintained upon salt stress in these hormone-related mutants (FIG. 10C). However, the ethylene insensitive ein2[19] and ein3 mutants[20] were strongly compromised in the beneficial effect of SA187, indicating that ethylene signaling is a major factor in this process.

Figure 10D:
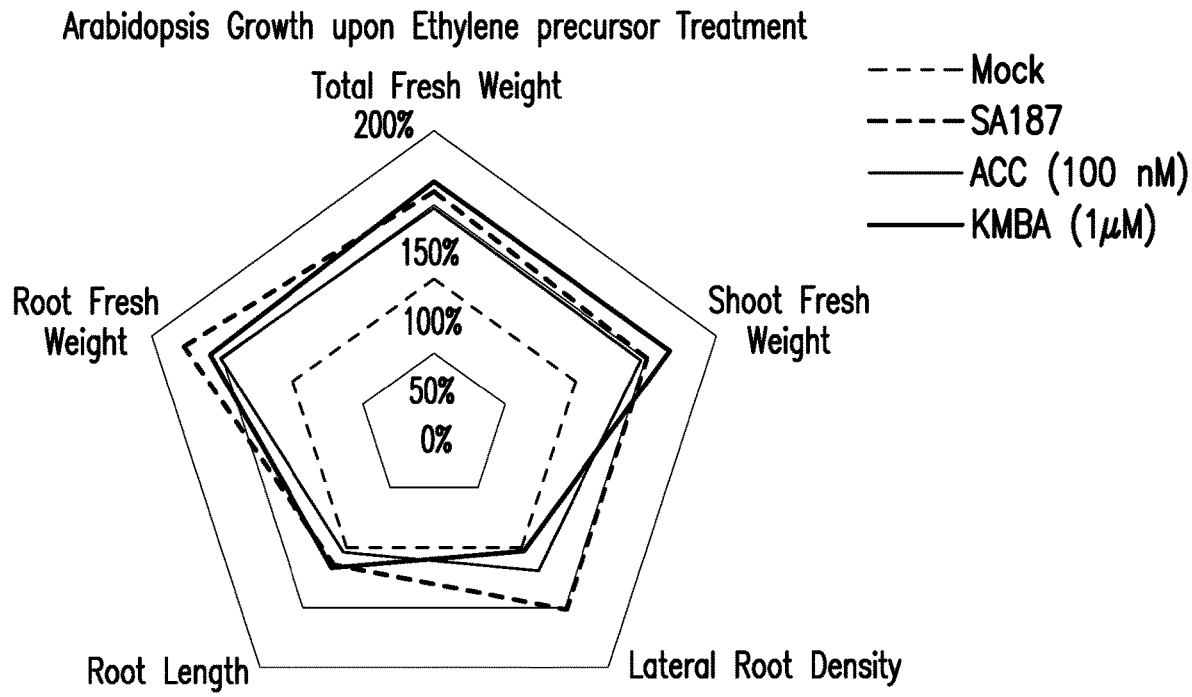
FIG. 10D is a graph showing 100 nM ACC and 1 μM KMBA partially mimic the beneficial effect of SA187 during salt stress treatment.

This result was validated by qPCR analysis of a number of ethylene-induced genes upon colonization by SA187 and by demonstrating the strong activation of the ethylene-dependent reporter EBF2::GUS in response to SA187 (data not shown). Moreover, application of the ethylene precursor ACC (100 nM) during salt stress could largely mimic the beneficial activity of SA187 on plants (FIG. 10D).

Figure 10E:
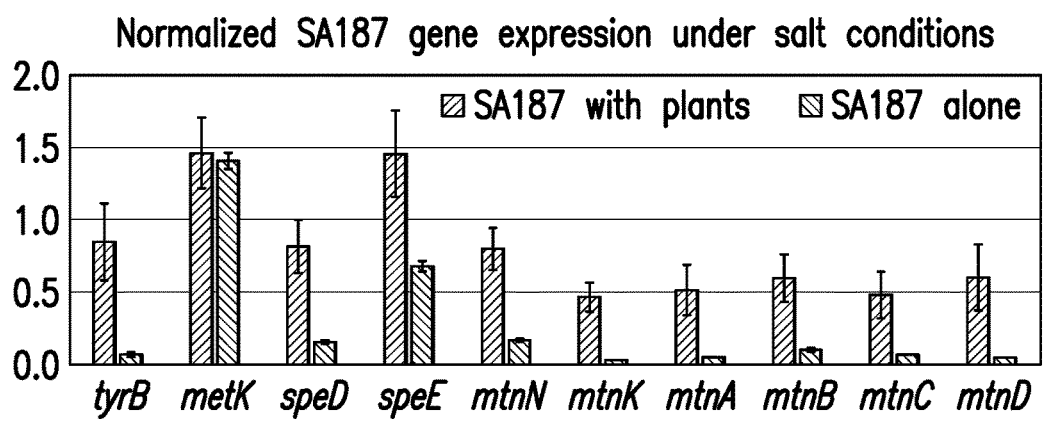
FIG. 10E shows qPCR analysis of expression of SA187 methionine salvage cycle genes under salt stress conditions: SA187-inoculated plants versus SA187 alone incubated in synthetic broth.
Figure 11:
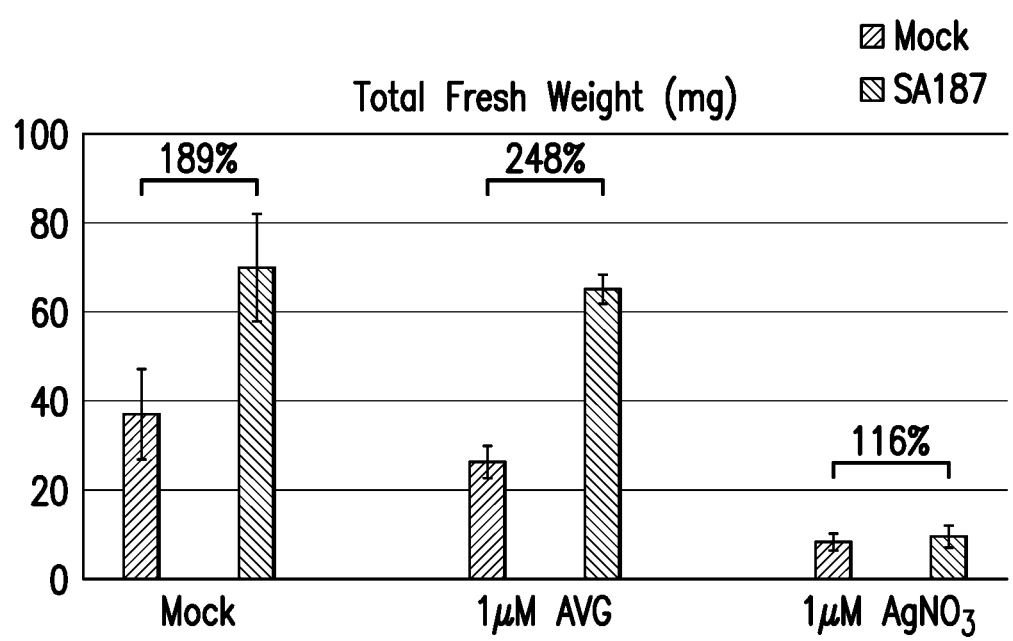
FIG. 11 is a bar graph of total fresh weight of 18-d-old *Arabidopsis* seedlings on medium with ethylene synthesis/signaling inhibitors. SD are displayed.

Surprisingly, the heptuple ethylene biosynthesis deficient mutant acs1-lacs2-lacs4-lacs5-2acs6-lacs7-lacs9-1 (hept acs)[21] still showed full sensitivity to the beneficial activity of SA187 (FIG. 10C). Moreover, SA187-beneficial effect is still existing while using the ethylene production inhibitor Amino ethoxyvinylglycine (AVG), however when they were treated with Silver nitrate ($AgNO_3$), an interferer of ethylene perception, SA187 lost its activity towards Arabidopsis (FIG. 11). This would suggest that ethylene production might not originate from plants but be derived from SA187 itself. To elucidate this question, we searched for ethylene forming enzyme (EFE)[22], or ACC Synthase genes in the genome of SA187, but no related genes were found. We confirmed our bioinformatic analysis by showing that SA187 does not produce ethylene when grown on synthetic media, However, some bacteria can indirectly produce ethylene via the production of KMBA, an intermediate of the methionine salvage pathway[23,24]. KMBA can spontaneously convert to ethylene by photo-oxidation or by peroxidases[25], which are rich in the plant apoplastic compartment. Interestingly, the KMBA pathway is completely conserved in SA187 and gene expression levels of most of the KMBA pathway enzymes were shown to be highly upregulated upon plant colonization compared with bacteria grown on synthetic medium (FIG. 10E).

To confirm that KMBA could function as an ethylene precursor during the beneficial plant-microbe interaction, different concentrations of KMBA were tested on Arabidopsis in the absence of SA187. As shown in FIG. 10D, a 100 nM KMBA concentration showed similar beneficial activity on salt stress tolerance on Arabidopsis plants as SA187 or ACC (FIG. 10D).

In summary, the endophytic bacteria Enterobacter sp. SA187 promotes plant tolerance to abiotic stresses. The capacity of SA187 to colonize both outer and inner tissues of Arabidopsis roots and shoots supports a functional interaction, using natural openings for internalization. Interestingly, based on transcriptomic and genetic evidences, it was demonstrated that SA187 beneficial activity is mediated by indirect production of ethylene through the production of KMBA, a pathway only activated when bacteria interact with plants. Although microbial PGPR activity is commonly attributed to a reduction of the plant ethylene contents through the activity of bacterial ACC deaminases[26-29], or independent of the ethylene signaling pathway[30,31], the role of ethylene in plant abiotic stress tolerance is not clear[32]. Up to now, only few reports hypothesized the involvement and activation of the ethylene signaling pathway to explain abiotic stress tolerance induction of rhizospheric bacteria, and are largely based on volatile emission or by comparison with plant-fungal interactions[12,33-35] These results strongly agree with those of Peng et al. (2014), where pretreatment with external ethylene or an EIN3/EIL1 gain-of-function mutant were sufficient to enhance salt stress tolerance[36]. Finally, an important outcome of this work is to show that SA187 can also promote biomass and yield increases on taxonomically unrelated plant crop species. These results show that the use of bacterial strains such as SA187 could provide an eco-friendly non-GMO solution for increasing agricultural production of many crops in a sustainable way.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11118159B2). An electronic copy of the "Sequence Listing" will also be available from the USPTO upon request and payment of the fee set forth in 37 CFR 1.19(b)(3).

We claim:

1. A method of improving growth of a seedling, seed or plant under abiotic stress conditions comprising:
   coating the seed or root of the plant with an effective amount of *Enterobacter* sp. SA187 to provide the plant with resistance to abiotic stress and/or
   growing the seedling, seed or plant in a plant substrate, wherein the plant substrate comprises an effective amount of SA187 to colonize the seed or a root of the plant to provide abiotic stress resistance to the seed or plant.

2. The method of claim 1, comprising inoculating the plant's rhizosphere with SA187.

3. The method of claim 1, wherein the plant substrate is selected from the group consisting of soil, peat, compost, vermiculite, perlite, sand, clay and combinations thereof.

4. The method of claim 1, wherein the abiotic conditions are selected from the group consisting of drought, high heat and high salt conditions.

5. The method of claim 1, further comprising contacting the plant with one or more additional plant growth-promoting bacteria.

6. The method of claim 1, comprising coating the seed or root of the plant with an effective amount of *Enterobacter* sp. SA187 to provide the plant with resistance to abiotic stress.

7. A method of improving growth of a seedling, seed or plant under abiotic stress conditions comprising, comprising growing the seedling, seed or plant in a plant substrate, wherein the plant substrate comprises an effective amount of *Enterobacter* sp. SA187 to colonize the seed or a root of the plant to provide abiotic stress resistance to the seed or plant.

8. The method of claim 7, wherein the plant substrate is selected from the group consisting of selected from a group consisting of soil, peat, compost, vermiculite, perlite, sand, clay and combinations thereof.

9. The method of claim 7, wherein the plant is selected from the group consisting of rice plant, maize, barley, lettuce, groundnuts, tomato, wheat, asparagus, chickpea, beans, and potato plant.

10. The method of claim 7, wherein the plant is *Nicotina tabacum, Avena sativa* or *Vitis vinifera*.

11. The method of claim 6, comprising coating the seed with a seed coating composition comprising SA187 at a concentration between $10^6$/ml to $10^9$/ml of seed coating composition.

* * * * *